United States Patent
Ando

(10) Patent No.: US 12,026,935 B2
(45) Date of Patent: Jul. 2, 2024

(54) IMAGE PROCESSING METHOD, TRAINING DEVICE, AND IMAGE PROCESSING DEVICE

(71) Applicant: OLYMPUS CORPORATION, Hachioji (JP)

(72) Inventor: Jun Ando, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 17/569,205

(22) Filed: Jan. 5, 2022

(65) Prior Publication Data

US 2022/0130136 A1   Apr. 28, 2022

Related U.S. Application Data

(63) Continuation of application No. PCT/JP2019/046692, filed on Nov. 29, 2019.

(51) Int. Cl.
*G06V 10/774* (2022.01)
*G06N 3/045* (2023.01)
(Continued)

(52) U.S. Cl.
CPC ........... *G06V 10/774* (2022.01); *G06N 3/045* (2023.01); *G06V 10/764* (2022.01);
(Continued)

(58) Field of Classification Search
CPC .. G06V 10/774; G06V 10/764; G06V 10/776; G06V 10/82; G06V 10/98;
(Continued)

(56) References Cited

U.S. PATENT DOCUMENTS 6,449,591 B1   9/2002   Kondo et al.
9,552,536 B2   1/2017   Ando
(Continued)

FOREIGN PATENT DOCUMENTS

JP   H04158482 A   6/1992
JP   H05280948 A   10/1993
(Continued)

OTHER PUBLICATIONS

Ex parte Quayle Office Action dated Jun. 8, 2022 issued in related U.S. Appl. No. 16/905,539.
(Continued)

*Primary Examiner* — Juan A Torres
(74) *Attorney, Agent, or Firm* — Holtz, Holtz & Volek PC

(57) ABSTRACT

An image processing method includes generating a first augmented image by applying first data augmentation on an input image, generating a second augmented image by applying second data augmentation on the input image, generating a first output by inputting the first augmented image to a neural network, generating a second output by inputting the second augmented image to the neural network, calculating an output difference indicating a degree of difference between the first output and the second output, and updating a weight coefficient of each layer of the neural network based on the output difference.

17 Claims, 13 Drawing Sheets

(51) Int. Cl.
   *G06V 10/764*   (2022.01)
   *G06V 10/776*   (2022.01)
   *G06V 10/82*    (2022.01)
   *G06V 10/98*    (2022.01)
   *G16H 30/40*    (2018.01)

(52) U.S. Cl.
   CPC ............ *G06V 10/776* (2022.01); *G06V 10/82* (2022.01); *G06V 10/98* (2022.01); *G16H 30/40* (2018.01); *G06V 2201/032* (2022.01)

(58) Field of Classification Search
   CPC .. G06V 2201/032; G06N 3/045; G06N 3/084; G16H 30/40; G16H 30/20; G16H 50/70; G16H 50/20; G06F 18/214; G06T 7/00
   USPC ......................................................... 382/128
   See application file for complete search history.

(56) References Cited

U.S. PATENT DOCUMENTS

| | | | |
|---|---|---|---|
| 10,753,997 | B2 * | 8/2020 | Odry ..................... G01R 33/543 |
| 2008/0279460 | A1 | 11/2008 | Kasahara et al. |
| 2011/0170769 | A1 | 7/2011 | Sakimura et al. |
| 2011/0176725 | A1 | 7/2011 | Homma et al. |
| 2015/0331832 | A1 | 11/2015 | Minoya et al. |
| 2016/0217368 | A1 | 7/2016 | Ioffe et al. |
| 2018/0211164 | A1 * | 7/2018 | Bazrafkan ............... G06N 3/045 |
| 2018/0373999 | A1 * | 12/2018 | Xu .......................... G06V 20/49 |
| 2019/0083180 | A1 | 3/2019 | Ichiki |
| 2019/0138838 | A1 | 5/2019 | Liu et al. |
| 2019/0164037 | A1 | 5/2019 | Kim et al. |
| 2020/0012932 | A1 | 1/2020 | Wang et al. |
| 2020/0012942 | A1 | 1/2020 | Ioffe et al. |
| 2020/0057924 | A1 | 2/2020 | Ioffe et al. |
| 2020/0065992 | A1 * | 2/2020 | Sung ....................... G06N 3/084 |
| 2020/0110994 | A1 * | 4/2020 | Goto ....................... G06N 3/044 |
| 2020/0234127 | A1 | 7/2020 | Ioffe et al. |
| 2020/0302171 | A1 * | 9/2020 | Kim ......................... G06F 17/16 |
| 2020/0320393 | A1 | 10/2020 | Ando |
| 2021/0117651 | A1 | 4/2021 | Kotake |
| 2021/0142512 | A1 | 5/2021 | Ando |

FOREIGN PATENT DOCUMENTS

| | | | |
|---|---|---|---|
| JP | 2008282267 | A | 11/2008 |
| JP | 2011145791 | A | 7/2011 |
| JP | 2011150541 | A | 8/2011 |
| JP | 2015215837 | A | 12/2015 |
| JP | 2017164007 | A | 9/2017 |
| JP | 2019003396 | A | 1/2019 |
| JP | 2019159958 | A | 9/2019 |
| WO | 2016123409 | A1 | 8/2016 |

OTHER PUBLICATIONS

International Search Report (ISR) (and English translation thereof) dated Feb. 10, 2020, issued in International Application No. PCT/JP2019/046692.

Krizhevsky, et al., "Imagenet Classification with Deep Convolutional Neural Networks", Advances in neural Information processing systems 25, pp. 1097-1105, (2012), Retrieved at URL: https://proceedings.neurips.cc/paper/2012/file/c399862d3b9d6b76c8436e924a68c45b-Paper.pdf.

Matsuoka, et al., "Deep similarity metric learning with unsupervised learning", The 79th National Convention of IPSJ, "2.1 Feature Extraction Unit", pp. 2-383 to 2-384, Mar. 16, 2017.

International Preliminary Report on Patentability (IPRP) (and English language translation thereof) dated Feb. 16, 2021 issued in International Application No. PCT/JP2018/030119.

International Preliminary Report on Patentability (IPRP) (and English language translation thereof) dated Jun. 23, 2020 issued in International Application No. PCT/JP2017/045573.

International Search Report (ISR) (and English translation thereof) dated Mar. 13, 2018 issued in International Application No. PCT/JP2017/045573.

International Search Report (ISR) (and English translation thereof) dated Nov. 13, 2018 issued in International Application No. PCT/JP2018/030119.

International Search Report (ISR) dated Jun. 3, 2014 issued in International Application No. PCT/JP2014/056886.

U.S. Appl. No. 16/905,539, First Named Inventor: Jun Ando; Title: "Data Processing Method and Data Processing Device", filed Jun. 18, 2020.

U.S. Appl. No. 17/151,719, First Named Inventor: Jun Ando; Title: "Image Processing Method and Image Processing Apparatus", filed Jan. 19, 2021.

Ioffe, et al., "Batch Normalization: Accelerating Deep Network Training by Reducing Internal Covariate Shift", arXiv:1502.03167v3 [cs.LG] Mar. 2, 2015, pp. 1-11.

Ren, et al., "Faster R-CNN: Towards Real-Time Object Detection with Region Proposal Networks", Conference on Neural Information Processing Systems (NIPS), 2015.

Office Action dated Nov. 27, 2023, issued in related U.S. Appl. No. 17/151,719.

Alsheakhali, "Machine Learning for Medical Instrument Detection and Pose Estimation in Retinal Microsurgery", (Doctoral dissertation, Technische Universität München). (Year: 2017).

Du, et al., "Articulated Multi-Instrument 2-D Pose Estimation Using Fully Convolutional Networks", IEEE Transactions on Medical Imaging. May 1, 2018;37(5): 1276-87. (Year: 2018).

Mwikirize, et al., "Convolution neural networks for real-time needle detection and localization in 2D ultrasound", International Journal of Computer Assisted Radiology and Surgery. May 2018; 13:647-57. (Year: 2018).

* cited by examiner

IMAGE PROCESSING METHOD, TRAINING DEVICE, AND IMAGE PROCESSING DEVICE

CROSS REFERENCE TO RELATED APPLICATION

This application is a continuation of International Patent Application No. PCT/JP2019/046692, having an international filing date of Nov. 29, 2019, which designated the United States, the entirety of which is incorporated herein by reference.

BACKGROUND

A method of performing various kinds of image processing using machine learning has been conventionally known. Examples of the image processing mentioned herein include an image classification process and an object detection process. A method of performing data augmentation in training processing of generating a trained model has also been known.

For example, Alex Krizhevsky, Ilya Sutskever, and Geoffrey E. Hinton: "Imagenet Classification with Deep Convolutional Neural Networks", Advances in neural information processing systems 25, pp. 1097-1105 (2012) discloses a method of applying a convolutional neural network (CNN) to large-scale image classification. In addition, Alex Krizhevsky, Ilya Sutskever, and Geoffrey E. Hinton: "Imagenet Classification with Deep Convolutional Neural Networks", Advances in neural information processing systems 25, pp. 1097-1105 (2012) discloses a method of performing data augmentation, such as random cropping, horizontal flipping, and color correction, to prevent overfitting.

SUMMARY

In accordance with one of some aspect, there is provided an image processing method comprising:
generating a first augmented image by applying first data augmentation on an input image;
generating a second augmented image by applying, on the input image, second data augmentation different from the first data augmentation;
generating a first output by inputting the first augmented image to a neural network;
generating a second output by inputting the second augmented image to the neural network;
calculating an output difference indicating a degree of difference between the first output and the second output; and
updating a weight coefficient of each layer of the neural network based on the output difference.

In accordance with one of some aspect, there is provided an image processing method using a neural network,
the neural network being trained using an error including a degree of difference between a plurality of outputs corresponding to a plurality of augmented images when the plurality of augmented images is input to the neural network, the plurality of augmented images being generated by application of a plurality of types of different data augmentation to one input image,
the method comprising:
generating a first application output by inputting a first application image to the neural network;
generating a first recognition result based on the first application output;
generating a second application output by inputting a second application image to the neural network; and
generating a second recognition result based on the second application output,
in a case where the first application image and the second application image correspond to a captured image of an object and a difference between the first application image and the second application image is at least one of a hue, brightness, or a smoothing level, the first recognition result and the second recognition result being identical.

In accordance with one of some aspect, there is provided a training device, comprising:
an interface configured to acquire an input image; and
a processor including hardware and performing machine learning based on the input image;
the processor
generating a first augmented image by applying first data augmentation on the input image,
generating a second augmented image by applying, on the input image, second data augmentation different from the first data augmentation,
generating a first output by inputting the first augmented image to a neural network,
generating a second output by inputting the second augmented image to the neural network,
calculating an output difference indicating a degree of difference between the first output and the second output, and
updating a weight coefficient of each layer of the neural network based on the output difference.

In accordance with one of some aspect, there is provided an image processing device, comprising:
a memory configured to store a trained model;
a processor including hardware and performing image processing on an application image based on the trained model,
the trained model being trained by
generating a first augmented image by applying first data augmentation on an input image,
generating a second augmented image by applying, on the input image, second data augmentation different from the first data augmentation,
generating a first output by inputting the first augmented image to a neural network,
generating a second output by inputting the second augmented image to the neural network,
calculating an output difference indicating a degree of difference between the first output and the second output, and
updating a weight coefficient of each layer of the neural network based on the output difference.

DESCRIPTION OF EXEMPLARY EMBODIMENTS

Figure 1:
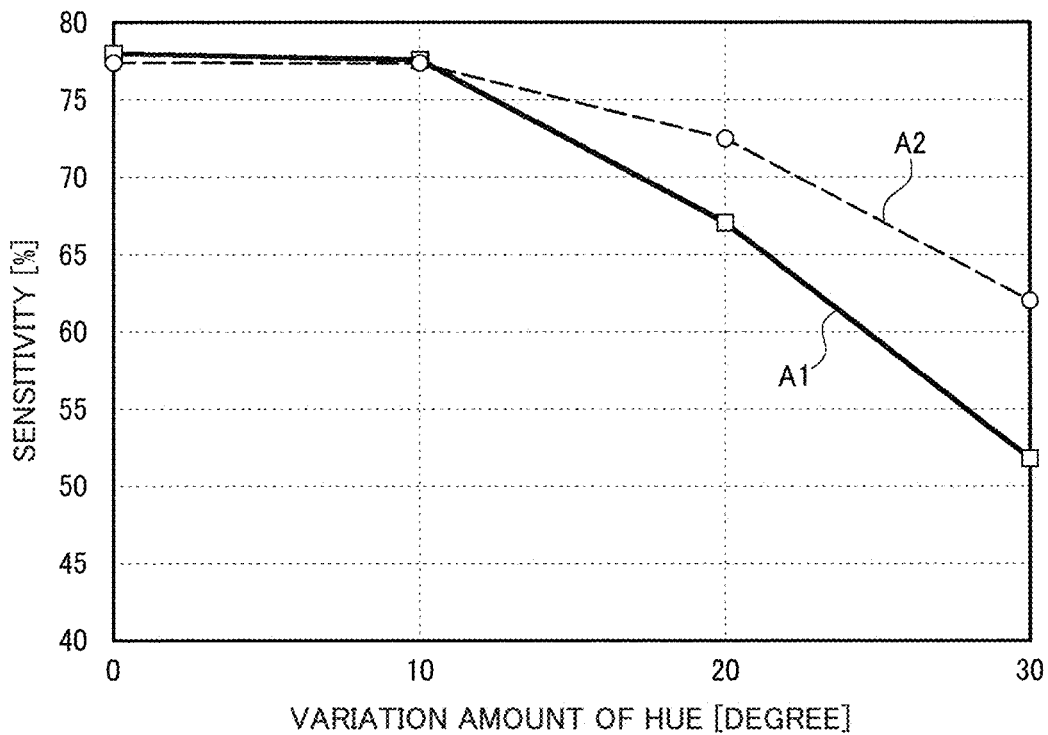
FIG. 1 is a diagram for describing that reduction in accuracy is prevented by a method in accordance with the present embodiment.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements

1. Method in Accordance with the Present Embodiment

In recent years, a method of performing an image classification process and an object detection process using machine learning has been widely known. The image classification process is a process of classifying an image into several categories, and is, for example, a process of classifying a main object of the image. Such an image classification process as to determine whether an object in an image is a cat or a dog has been widely known. The object detection process is a process of determining a category of an object in an image and also determining a position of the object in the image. For example, known are a method of detecting a region surrounding an object of a given category, a method of determining, with respect to each pixel of an image, to which category of an object the pixel corresponds, and other methods. The image classification process and the object detection process are hereinafter collectively referred to as a recognition process on an image.

As disclosed in Alex Krizhevsky, Ilya Sutskever, and Geoffrey E. Hinton: "Imagenet Classification with Deep Convolutional Neural Networks", Advances in neural information processing systems 25, pp. 1097-1105 (2012) and the like, a recognition process using a deep-learning technique uses a method of inputting an image to a trained neural network to output a score representing a probability of being a recognition target and deciding a final recognition result based on the score.

In a case where variations in shade of color, lightness, smoothing level, or the like occur in an image serving as an input, there is a possibility that a score output from a trained model largely varies even if the variations are small. Since the neural network, in particular, is composed of linearly coupled multi-layers as described later with reference to FIGS. 5A and 5B, there is a possibility that an output score largely changes due to small variations in the input. That is, there is a possibility that a recognition result becomes different due to small variations in shade of color or the like, and the recognition result becomes unstable. To address this, the present embodiment uses data augmentation by performing a color correction process, a brightness correction process, a smoothing process, or the like to generate augmented images whose number is padded. Performing training using an image set including augmented images as training data can increase accuracy in processing using a trained model.

However, careful examination needs to be given to a range of data augmentation, specifically, a lower limit value and upper limit value of a parameter used in data augmentation. A description will be given using an example of a case where the data augmentation is the color correction process. The color correction process is, for example, a process of changing a hue H of an image. A parameter of the data augmentation in this case is a variation amount $\Delta H$ of the hue. Assume that data augmentation is performed so that $\Delta H$ becomes a value within a range of $-10$ degrees$\leq \Delta H \leq 10$ degrees.

FIG. 1 is a diagram for describing a change in results of the recognition process in a case where a variation amount of a test image is changed. The test image is an image for checking accuracy of an inference process using the trained model, and is an image to which a correct label is attached in a more limited sense. The inference process mentioned herein is the recognition process as described above, and the correct label is information that identifies a category or position of an object serving as the recognition target. An abscissa axis in FIG. 1 represents a variation amount of the hue H added to the test image. An ordinate axis in FIG. 1 represents sensitivity. The sensitivity mentioned herein is a ratio of the number of recognition targets correctly detected in the recognition process using the trained model to the number of recognition targets existing in the test image. That is, the diagram indicates that the recognition process can be performed with higher accuracy as the sensitivity becomes higher.

A1 in FIG. 1 represents a recognition result in accordance with a conventional method. As illustrated in A1, in a case where a variation amount of the test image is ±10 degrees, the sensitivity becomes a value as high as a value in a case where the variation amount is 0 degrees. In contrast, in a case where the variation amount of the test image becomes ±20 degrees, the sensitivity decreases. In a case where the variation amount of the test image becomes ±30 degrees, the sensitivity further decreases. As can be found from A1 is FIG. 1, in a case where the variation amount of the test image is within a range of a variation amount assumed in the data augmentation, the recognition process can be performed with sufficiently high accuracy. On the other hand, in a case where the variation amount of the test image is larger than the variation amount assumed in the data augmentation, the accuracy of the recognition process is reduced significantly.

While the description has been given of the example using the test image having a known answer with reference to FIG. 1, the same can apply to the recognition process targeting an unknown image acquired in an actual environment. Additionally, the description has also been given of the accuracy of the recognition process with reference to FIG. 1, the same applies to a case of applying the trained model to image processing other than the recognition process. That is, it is preferable that a range of a parameter in the data augmentation be set to cover a variation amount of an image in the actual environment. The image acquired in the actual environment and serving as a target for the inference process to which the trained model is applied is hereinafter referred to as an application image.

However, there are many cases where the variation amount of the application image is difficult to be acquired. For example, consideration will be given of a case of installing a function of performing the inference process using the trained model in a new-type endoscope apparatus (endoscope system). There is a possibility that the new-type endoscope apparatus is different from an old-type endoscope apparatus in configurations of, for example, an image sensor, a light source, a lens, and the like, and a tendency of an image to be captured is different. Hence, generation of a trained model dedicated to the new-type endoscope apparatus is considered to contribute to an increase of accuracy. However, since an in-vivo image cannot be captured unless an insertion section of the endoscope apparatus is inserted into the inside of a living body, it is difficult to acquire a large number of images captured using the new-type endoscope apparatus at a manufacturing stage of the endoscope apparatus. Hence, it is realistic to reuse a trained model that has undergone the machine learning using images captured by the old-type endoscope apparatus in the new-type endoscope apparatus until a sufficient number of images for training are accumulated. However, given that it is difficult to acquire a large number of images captured by the new-type endoscope apparatus as described above, it is difficult to predict the variation amount of the image in a case of using the new-type endoscope apparatus. That is, there is a possibility that even if the data augmentation is attempted to absorb a difference between the new-type endoscope apparatus and the old-type endoscope apparatus, a parameter used in the data augmentation is difficult to be set. As a result, there is a possibility that the accuracy of the image processing such as the recognition process decreases. While the endoscope apparatus is herein exemplified, there is a case where a user's imaging environment is not easy to be predicted correctly at the time of execution of the machine learning in a general digital still camera or the like. Also in this case, it is difficult to predict the variation amount of the image in the actual environment.

In consideration of the above issues, the present embodiment executes the following processing. An image processing method in accordance with the present embodiment includes generating a first augmented image by applying first data augmentation on an input image, and generating a second augmented image by applying, on the input image, second data augmentation different from the first data augmentation. The method in accordance with the present embodiment further includes generating a first output by inputting the first augmented image to a neural network, and generating a second output by inputting the second augmented image to the neural network. The method then includes calculating an output difference indicating a degree of difference between the first output and the second output, and updating a weight coefficient of each layer of the neural network based on the output difference. More specifically, the weight coefficient is updated in such a way as to reduce the output difference.

Specifically, the image processing method in accordance with the present embodiment includes generating the trained model for executing the image processing on the application image. That is, in the image processing method in accordance with the present embodiment, the trained model is output as a result of repeated execution of a process of generating the first augmented image and the second augmented image, a process of generating the first output and the second output, a process of calculating the output difference, and a process of updating the weight coefficient based on the output difference. For example, the trained model is output to an image processing device 40, which will be described later with reference to FIG. 13, and the image processing device 40 executes the image processing on the application image using the trained model, for example, a recognition process for a target object.

Since the first augmented image and the second augmented image are images to which different types of data augmentation are applied, a hue, lightness, or the like of one of the first augmented image and the second augmented image varies from the other thereof. Hence, in accordance with the conventional method, there is a possibility that the first output and the second output are significantly different from each other. In accordance with the present embodiment, however, the machine learning is performed so as to reduce a difference between the first output and the second output. Consequently, the present embodiment prevents a major change in score to be output due to small variations in the input, and can thereby stabilize a recognition result. In other words, the present embodiment can increase robustness with respect to variations in the image input to the neural network. That is, even in a case of observing a peculiar symptom or a polyp not from its front side but from an oblique direction at the time of inputting an endoscopic image to the neural network and detecting the polyp, accuracy in recognition becomes hard to be reduced.

A2 in FIG. 1 represents a result of the recognition process in a case of applying the method in accordance with the present embodiment. In a case where the variation amount of the test image is ±10 degrees, the sensitivity is at a similar level to that in the conventional method indicated in A1. In a case where the variation degree in the test image is ±20 degrees or ±30 degrees, however, an amount of reduction in sensitivity is made small as compared with the conventional method as illustrated in A2. That is, even in a case where the variation amount of the image in the actual environment exceeds the range of data augmentation due to unpredictability of the variation amount, the method in accordance with the present embodiment can prevent reduction in accuracy of the image processing using the trained model.

In addition, the method in accordance with the present embodiment can be applied to an image processing method using a neural network, which is a generated trained model. The neural network mentioned herein is trained using an error including a degree of difference between a plurality of outputs corresponding to a plurality of augmented images when the plurality of augmented images is input to the neural network. The plurality of augmented images is generated by applying a plurality of different types of data augmentation to one input image. The image processing method includes generating a first application output by inputting a first application image to the neural network, and generating a first recognition result based on the first application output. In addition, the image processing method includes generating a second application output by inputting a second application image to the neural network, and generating a second recognition result based on the second application output. In a case where an image of a corresponding object is captured in the first application image and the second application image and a difference between the first application image and the second application image corresponds to at least one of a shade of color, lightness, or a smoothing level, a difference between the first recognition result and the second recognition result is identical or substantially identical in the image processing method in accordance with the present embodiment. Being substantially identical means that the difference between the first recognition result and the second recognition result is equal to or smaller than a given threshold. The shade of color is, for example, a hue. The lightness is, for example, luminance or brightness. The smoothing level is, for example, a contrast value or the like.

Note that the first application output is an output of the neural network in a case where the first application image is input to the neural network. For example, in a case where an output layer of the neural network is a known softmax layer, the first application output is probability data indicating a probability that a recognition result is a given object. The same applies to the second application output. The first recognition result is information obtained based on the first application output. For example, the first recognition result is acquired by selection of probability data having the largest value from a plurality of pieces of probability data corresponding to the first application output. For example, in a case where an image classification process of classifying objects into a polyp and an object other than the polyp, the first application output is two numerical values, one corresponding to probability data indicating a probability of being the polyp and the other corresponding to probability data indicating a probability of being the object other than the polyp. Whether or not an object is the polyp is determined on the basis of which value is larger. The same applies to the second application output and the second recognition result.

As described above, even if variations in shade of color, lightness, and smoothing level of the input application image occur, the method in accordance with the present embodiment reduces a difference in outputs in the neural network. Hence, the present embodiment makes a difference between the first application output and the second application output sufficiently small. When a recognition result is obtained from application outputs, there are many cases where a minute difference in application outputs does not become a problem. For example, in a case where a maximum value of the probability data is obtained as described above, the recognition result indicates the polyp with any number of specific numerical values, only if a condition that the probability data indicating the probability of being the polyp has a larger value than that of the probability data indicating the probability of being the object other than the polyp is satisfied. That is, in a training processing method in accordance with the present embodiment, the first recognition result and the second recognition result are identical.

In a case where the object detection process is performed, however, a detection result is, for example, a rectangular region surrounding the object. While the recognition result of the image classification process is a crude recognition result indicating whether or not the object is the polyp, the position and size of the rectangular region, which is the recognition result of the object detection process, are detected with a finer grain size. While a specific grain size depends on a model of the neural network, the present embodiment can perform detection, for example, on a pixel-by-pixel basis. In a case of performing segmentation, the present embodiment determines to which object a pixel corresponds, on the pixel-by-pixel basis. In the case of the object detection process, assumed is a case where the difference between the first application output and the second application output is not sufficiently absorbed because the recognition result is fine, and the first recognition result and the second recognition result do not become identical. However, since the difference between the first application output and the second application output is reduced, the first recognition result and the second recognition result are expected to be substantially identical. For example, in a case where the recognition result represents the rectangular region, a difference in position or size is equal to or smaller than a predetermined number of pixels. Alternatively, in a case where the object is identified by pixel unit, the number of pixels in which the identified object is different between the first recognition result and the second recognition result is equal to or smaller than a predetermined number of pixels.

2. System Configuration Example

Figure 2:
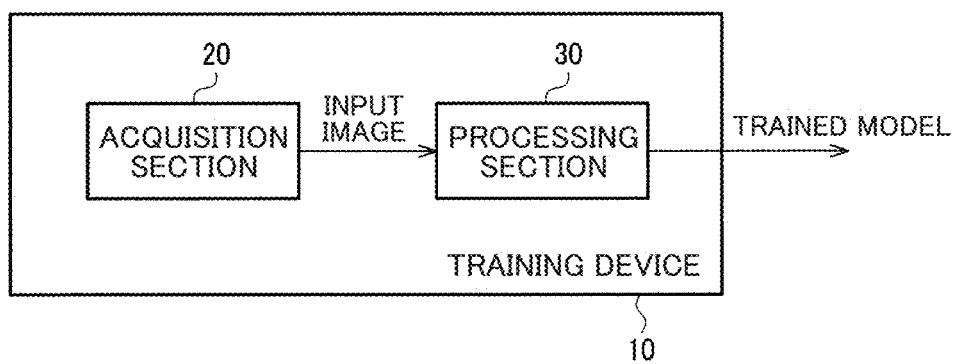
FIG. 2 illustrates a configuration example of a training device.

The method in accordance with the present embodiment may be applied to a training device 10. As illustrated in FIG. 2, the training device 10 includes an acquisition section 20 that acquires an input image, and a processing section 30 that performs the machine learning based on the input image. However, the training device 10 is not limited to a configuration illustrated in FIG. 2, and can be modified in various manners, such as omission of part of constituent elements and addition of other constituent elements.

The acquisition section 20 acquires an input image used for the machine learning. The acquisition section 20 also acquires a correct label in correspondence with the input image. For example, an external device attaches the correct label to the input image, and the acquisition section 20 acquires the input image and the correct label from the external device. The acquisition section 20 in this case is a communication interface that communicates with the external device. Alternatively, the training device 10 attaches the correct label to the input image, and may include a storage section that is not illustrated and that accumulates attachment results. The acquisition section 20 in this case is an interface for reading out the input image to which the correct label is attached from the storage section. The storage section mentioned herein stores various kinds of information such as data and a program. The storage section may be a semiconductor memory, a register, a magnetic storage device, or an optical storage device.

The processing section 30 is configured by the following hardware. The hardware can include at least one of a circuit that processes a digital signal or a circuit that processes an analog signal. For example, the hardware can be composed of one or more circuit devices mounted on a circuit board, or one or more circuit elements. The one or more circuit devices are, for example, integrated circuits (ICs) or the like. The one or more circuit elements are, for example, resistors, capacitors, or the like.

In addition, the processing section 30 may be implemented by the following processor. The training device 10 in accordance with the present embodiment includes a memory that stores information, and a processor that operates based on the information stored in the memory. The information is, for example, a program, various kinds of data, and the like. The processor includes hardware. As the processor, various kinds of processors, such as a central processing unit (CPU), a graphics processing unit (GPU), and a digital signal processor (DSP), may be used. The memory may be a semiconductor memory such as a static random access memory (SRAM) and a dynamic random access memory (DRAM), a register, a magnetic storage device such as a hard disk drive (HDD), or an optical storage device such as an optical disk device. For example, the memory stores a computer-readable instruction. A function of each section of the processing section 30 is implemented as processing when the processor executes the instruction. The instruction mentioned herein may be an instruction set that is included in a program, or may be an instruction that instructs a hardware circuit included in the processor to operate.

The processing section 30 executes each of a process of generating the first augmented image, a process of generating the second augmented image, a process of generating the first output, a process of generating the second output, a process of calculating the output difference, and a process of updating the weight coefficient of each layer in the neural network.

Figure 3:
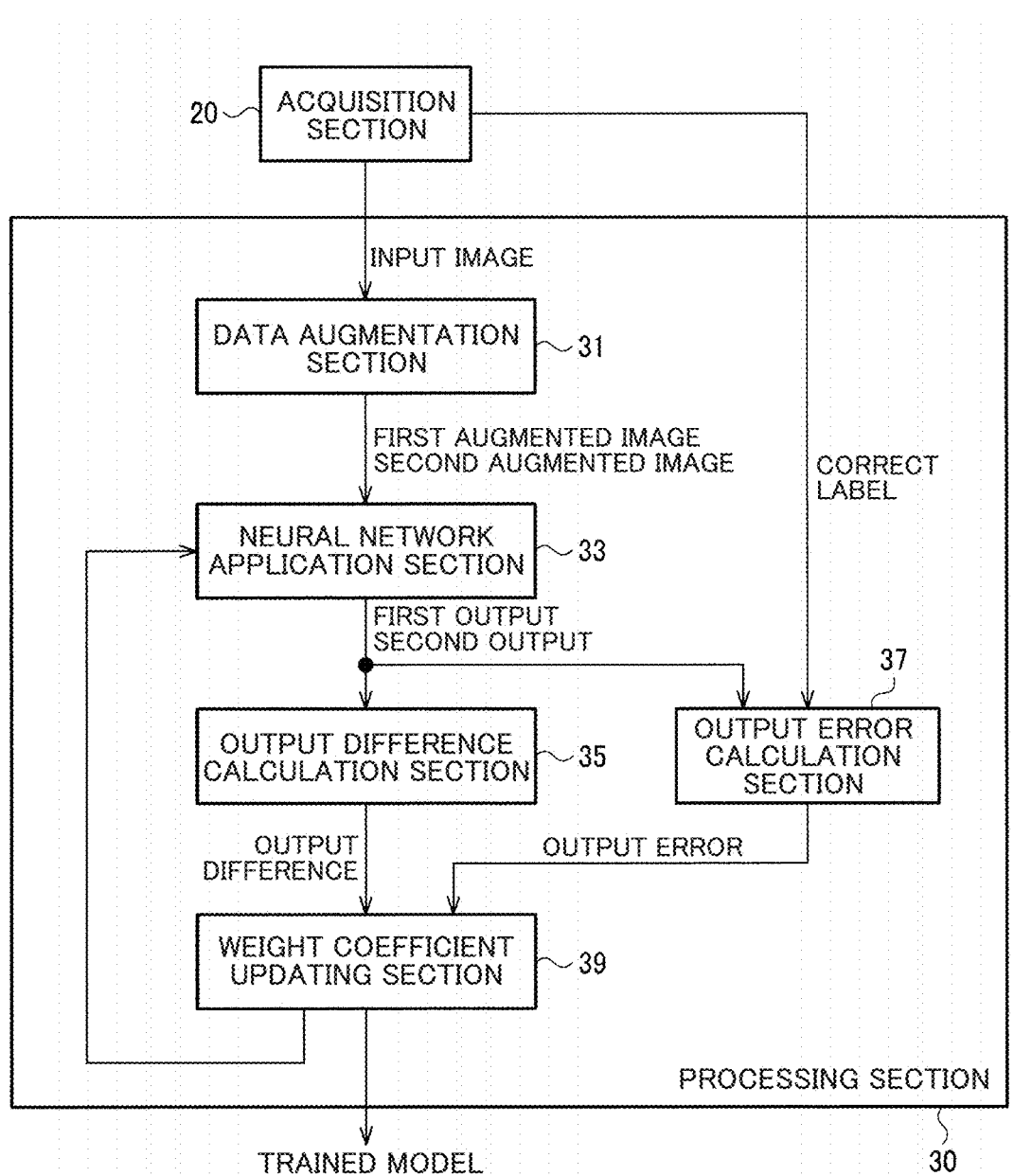
FIG. 3 illustrates a detailed configuration example of a processing section.

FIG. 3 illustrates a detailed configuration example of the processing section 30. The processing section 30 includes a data augmentation section 31, a neural network application section 33, an output difference calculation section 35, an output error calculation section 37, and a weight coefficient updating section 39. However, the processing section 30 is not limited to the configuration illustrated in FIG. 3, and can be modified in various manners, such as omission of part of constituent elements and addition of other constituent elements. For example, the processing section 30 may further include a constituent element such as an initialization section that initializes the neural network at the time of start of the machine learning.

The data augmentation section 31 acquire an input image from the acquisition section 20, and applies data augmentation to the input image. The data augmentation section 31 performs a process of generating the first augmented image by applying the first data augmentation to the input image, and a process of generating the second augmented image by applying the second data augmentation to the input image. The data augmentation section 31 outputs the first augmented image and the second augmented image to the neural network application section 33.

The neural network application section 33 performs a process of generating the first output by inputting the first augmented image to the neural network, and a process of generating the second output by inputting the second augmented image to the neural network. The neural network application section 33 outputs the first output and the second output to the output difference calculation section 35 and the output error calculation section 37.

The output difference calculation section 35 calculates the output difference based on the first output and the second output. The output difference calculation section 35 outputs the output difference to the weight coefficient updating section 39.

The output error calculation section 37 acquires the correct label corresponding to the input image from the acquisition section 20. The output error calculation section 37 calculates the output error based on the first output, the second output, and the correct label. The output error calculation section 37 outputs the output error to the weight coefficient updating section 39. Note that the output error may be an error based on the first output and the correct label, may be an error based on the second output and the correct label, or may include both of these errors.

The weight coefficient updating section 39 updates the weight coefficient of each layer of the neural network based on an overall error including the output difference. Note that the overall error may include the output difference and the output error.

Note that part or most of processing executed by the training device 10 in accordance with the present embodiment, the image processing device 40, which will be described later, and the like, may also be implemented by a program. In this case, the training device 10 or the like in accordance with the present embodiment is implemented by a processor such as a CPU executing the program. Specifically, the program stored in a non-transitory information storage device is read out and the readout program is executed by the processor such as the CPU. The information storage device mentioned herein stores a program, data, and the like, and functions thereof can be implemented by an optical disk such as a digital versatile disk (DVD) and a compact disk (CD), a hard disk drive (HDD), a memory such as a non-volatile memory and a random-access memory (RAM), or the like. The information storage device is a computer-readable device. The processor such as the CPU performs various kinds of processing of the present embodiment based on the program stored in the information storage device. That is, the information storage device stores the program causing a computer to function as each section of the present embodiment. The computer is a device including an operation section, a processing section, a storage section, and an output section.

3. Details of Processing

Figure 4:
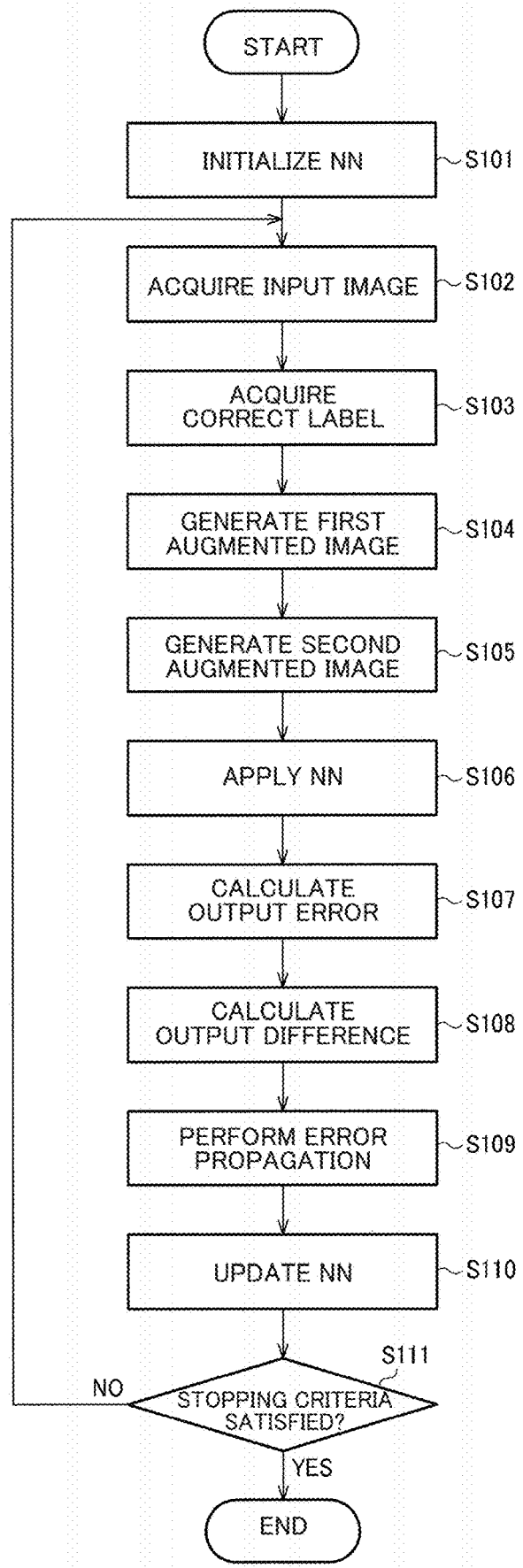
FIG. 4 is a flowchart describing training processing.

FIG. 4 is a flowchart describing training processing in accordance with the present embodiment. When this processing is started, in step S101, a process of initializing the neural network is first performed. Note that the neural network is denoted by NN as appropriate in the drawings.

Figure 5A:
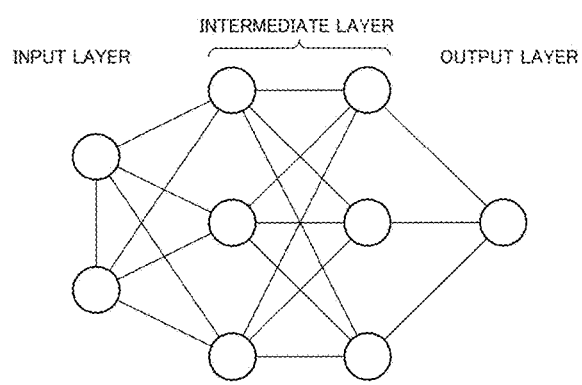
FIGS. 5A and 5B are diagrams for describing a neural network.

FIG. 5A is a schematic diagram for describing the neural network. The neural network includes an input layer that takes an input of data, an intermediate layer that performs calculation based on an output from the input layer, and an output layer that outputs data based on the output from the intermediate layer. In FIG. 5A, a network including the intermediate layer composed of two layers is exemplified, but may be the intermediate layer may be composed of one layer, or three or more layers. The number of nodes included in each layer is not limited to that in an example illustrated in FIG. 5A, and can be modified in various manners. Note that in consideration of accuracy, training in accordance with the present embodiment is preferably performed using a multi-layer neural network. The multi-layer mentioned herein means that four or more layers in a more limited sense.

As illustrated in FIG. 5A, a node included in a given layer is coupled to a node in an adjacent layer. A weight is set to each coupling. Each node is multiplied by an output and weight of a node in a former stage, and a total value of multiplication is obtained. Furthermore, with respect to each node, an output from the node is obtained by addition of a bias to the total value and application of an activating function to an addition result. Outputs from the neural network are obtained by sequential execution of this process from the input layer to the output layer. The training in the neural network is a process of deciding an appropriate weight coefficient. The weight coefficient mentioned herein includes the weight and bias described above. Various kinds of methods for the training, such as backpropagation, have been known, and a wide range of these methods can be applied to the present embodiment.

More specifically, the neural network in accordance with the present embodiment is a convolutional neural network (hereinafter referred to as CNN). Using the CNN enables generation of a preferable trained model for image processing.

Figure 5B:
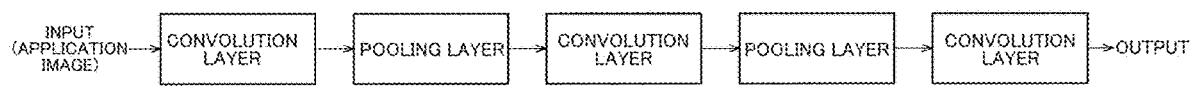

FIG. 5B is a schematic diagram for describing the CNN. The CNN includes a convolution layer that performs convolution calculation and a pooling layer. The convolution layer is a layer that performs filter processing. The pooling layer is a layer that reduces a size in a vertical direction and a size in a lateral direction. In an example illustrated in FIG. 5B, the CNN is a network that causes the convolution layer and the pooling layer to each perform calculation a plurality of times. Although not clearly illustrated in FIG. 5B, a calculation process using the activating function is also performed similarly to the example in FIG. 5A. The CNN in accordance with the present embodiment may include calculation by a fully connected layer. The fully connected layer is a layer that performs a calculation process in a case where all nodes included in the former layer are coupled to corresponding nodes in the given layer, and the calculation process corresponds to calculation in each layer described above with reference to FIG. 5A. In addition, the known softmax layer may be used as the output layer. A specific configuration of the CNN can be modified in various manners. The weight coefficient of the convolution layer of the CNN is a parameter of a filter. That is, the training in the CNN includes training of a filter used for the convolution calculation.

The present embodiment may also use, for example, a CNN based on VGG-16 as the neural network. Alternatively, the present embodiment may use a residual network that introduces identity mapping (IM) as the CNN. Various kinds of CNNs other than the above have been known, and a wide range of these CNNs can be applied to the present embodiment. Since the VGG-16 and the residual network are known methods, and a detailed description thereof is omitted.

Initialization of the CNN in step S101 is executed, for example, using a normal random number with a mean value of 0 and a standard deviation of wscale/√(ci×k×k). Note that wscale is a scale parameter, ci is the number of input channels of the convolution layer, and k is a convolutional kernel size. As an initial value of the weight coefficient of the convolution layer, a weight coefficient of a convolution layer that has been trained using a large-scale image database that is different from an image database used in the present embodiment may also be used. This enables high-performance training even in a case where the number of input images is small. Note that the image database in accordance with the present embodiment is a database including a plurality of input images, and is, for example, an aggregate of captured images of polyps.

Subsequently, in steps S102 and S103, the acquisition section 20 acquires an input image, and acquires a correct label in correspondence with the input image. In a case where the image classification process is performed, the correct label is binary data indicating whether or not a target of each classification category is included in an image. In a case where the object detection process is performed, the correct label is, for example, information that identifies a rectangular region including a detection target. The information that identifies the rectangular region may be a set of one coordinate value, a vertical size, and a lateral size, or may be a set of two coordinate values on a diagonal line. Alternatively, the correct label may be an array of binary data indicating whether or not the detection target is included on each candidate frame corresponding to each point on the image. Additionally, the neural network in accordance with the present embodiment may perform an image conversion process on the input image. The correct label in this case is an image as an ideal conversion result.

Subsequently, in step S104, the data augmentation section 31 generates the first augmented image by applying the first data augmentation to the input image. The first data augmentation includes at least one of the color correction process, the brightness correction process, the smoothing process, an image sharpening process, a noise addition process, or an affine transformation process. That is, the first data augmentation may be any one of these processes, or may be a combination of two or more of these processes.

The color correction process is, for example, a correction process of the hue H. The data augmentation section 31 converts red, green, and blue (RGB) pixel values to a hue, saturation and value (HSV) color space based on the following Expression (1). H represents a hue, S represents saturation, and V represents brightness (value). R, G, and B in the following Expression (1) represents respective pixel values for red, green, blue of the input image. Max represents a maximum value of the RGB pixel values, and Min represents a maximum value of the RGB pixel values.

[Expression 1]

$$H = \begin{cases} \frac{G-B}{\text{Max}-\text{Min}} \times 60 \, (\text{Max}=R) \\ \frac{B-R}{\text{Max}-\text{Min}} \times 60 + 120 (\text{Max}=G) \\ \frac{R-G}{\text{Max}-\text{Min}} \times 60 + 240 (\text{Max}=B) \end{cases} \quad (1)$$

$$S = \frac{\text{Max}-\text{Min}}{\text{Max}}$$

$$V = \text{Max}$$

The data augmentation section 31 performs a process of changing a calculated H by ΔH. ΔH mentioned herein is a parameter in the color correction process, and a value of ΔH is determined at random in a range of equal to or larger than a lower limit value and equal to or smaller than an upper limit value. In a case where the lower limit value is −10 degrees and the upper limit value is +10 degrees, any one value out of integer values that are equal to or larger than −10 and equal to or smaller than +10 is selected as ΔH. As described above, since the method in accordance with the present embodiment prevents reduction in accuracy even if the variation amount of the image in the actual environment exceeds the variation amount in the data augmentation, there is no need for excessively widening the range of the parameter.

The brightness correction process, is, for example, a gamma correction process. For example, the data augmentation section 31 performs the gamma correction process on the brightness V based on the following Expression (2). V represents brightness after the gamma correction process. In a case where γ is 1, original brightness is maintained. The larger γ is, the lower the brightness becomes. The smaller γ is, the higher the brightness becomes. The γ is a parameter in the brightness correction process. The data augmentation section 31 performs the gamma correction process by deciding a value of γ at random in the range of equal to or larger than the lower limit value and equal to or smaller than the upper limit value.

[Expression 2]

$$V' = \left(\frac{V}{255}\right)^\gamma \times 255 \quad (2)$$

Note that after performing the color correction process or the gamma correction process, the data augmentation section 31 performs reconversion to RGB pixel values based on the following Expression (3). R', G', and B' in the Expression (3) represent red, green, and blue pixel values after the reconversion, and floor (x) represents a maximum integer of equal to or smaller than x.

[Expression 3]

$$R' = \begin{cases} V'(h=0) \\ q(h=1) \\ p(h=2) \\ p(h=3) \\ t(h=4) \\ V'(h=5) \end{cases} \quad (3)$$

$$G' = \begin{cases} t(h=0) \\ V'(h=1) \\ V'(h=2) \\ q(h=3) \\ p(h=4) \\ p(h=5) \end{cases}$$

$$B' = \begin{cases} p(h=0) \\ p(h=1) \\ t(h=2) \\ V'(h=3) \\ V'(h=4) \\ q(h=5) \end{cases}$$

$$h = \text{floor}\left(\frac{H}{60}\right) f = \frac{H}{60} - h$$
$$p = V' \times (1 - S)$$
$$q = V' \times (1 - S \times f)$$
$$t = V' \times (1 - S \times (1 - f))$$

The smoothing process is, for example, a filter process using a smoothing filter. The smoothing filter is, for example, a filter that has a variable smoothing level. The smoothing level is, for example, a value of σ in a Gaussian filter. The lager σ is, the higher the smoothing level becomes. The σ mentioned herein is a parameter in the smoothing process. Note that various kinds of smoothing filters and various kinds of parameters that decide the smoothing level of the smoothing filter are known, and a wide range of the filters and parameters can be applied to the present embodiment. The data augmentation section 31 decides a parameter in the smoothing process in the range of equal to or larger than the preset lower limit value and equal to or smaller than the preset upper limit value, and executes the smoothing process identified by the parameter.

Alternatively, the smoothing filter is, for example, a filter having a fixed smoothing level, and the data augmentation section 31 may decide the number of times of application of the smoothing filter at random to change the smoothing level. In this case, the number of times of application is a parameter in the smoothing process. The smaller the number is, the lower the smoothing level becomes. For example, the smoothing level can be adjusted depending on how many times the Gaussian filter with fixed σ is used.

The image sharpening process is a filter process using an image sharpening filter such as an edge enhancement filter. With respect to the image sharpening filter, changing a parameter of the filter or the number of times of application of the filter can change an image sharpening level. That is, the parameter of the filter or the number of times of application is a parameter in the image sharpening process. The data augmentation section 31 decides the parameter in the image sharpening process in the range of equal to or larger than the preset lower limit value and equal to or smaller than the preset upper limit value, and executes the image sharpening process identified by the parameter.

The noise addition process is a process of adding a noise component to the input image. For example, performing the filter process using the Gaussian filter enables execution of a process of adding Gaussian noise. That is, the smoothing process described above can be considered as one aspect of the noise addition process. In this case, σ and the number of application of the filter is a parameter in the noise addition process. The noise addition process may be a process of adding impulse noise. For example, the data augmentation section 31 performs a process of changing pixel values of pixels in a predetermined ratio of the input image to a maximum value or a minimum value to add impulse noise to the input image. In a case where a pixel value is eight-bit data, the maximum value is 0, and the maximum value is 255. In this case, the ratio of pixels whose pixel values are to be changed is a parameter in the noise addition process, and changing the parameter can adjust a noise addition level. Besides this process, various kinds of noise addition processes on an image are widely known, and a wide range of these processes can be applied to the present embodiment. The data augmentation section 31 decides the parameter in the noise addition process in the range of equal to or larger than the preset lower limit value and equal to or smaller than the preset upper limit value, and executes the noise addition process identified by the parameter.

The affine transformation process is a process of performing resizing, rotation, and parallel movement of the image. Specifically, the data augmentation section 31 performs matrix calculation. Changing a value of each element in a matrix used for affine transformation can adjust a resizing rate, a rotation angle, and an amount of parallel movement. That is, the element of the matrix is a parameter in the affine transformation. Note that it is known that the matrix can be divided into a plurality of matrices in the affine transformation, and an element in each matrix may be alternatively used as a parameter. The data augmentation section 31 decides the parameter in the affine transformation process in the range of equal to or larger than the preset lower limit value and equal to or smaller than the preset upper limit value, and executes the affine transformation process identified by the parameter. Note that in the affine transformation of the present embodiment, not all of resizing, rotation, and parallel movement need to be performed. Any one of resizing, rotation, and parallel movement may be performed or two of resizing, rotation, and parallel movement may be performed in combination.

Performing such data augmentation enables generation of an augmented image including recognition targets having a variety of shades of colors, lightness, smoothing levels, image sharpness levels, noise amounts, sizes, angles, and positions on the image.

In step S105, the data augmentation section 31 generates the second augmented image by applying the second data augmentation to the input image. The second data augmentation includes at least one of the color correction process, the brightness correction process, the smoothing process, the image sharpening process, the noise addition process, or the affine transformation process. That is, the data augmentation section 31 performs image conversion of a similar type to that performed in step S104 as the second data augmentation. However, the data augmentation section 31 generates the second augmented image that is different from the first augmented image by changing a parameter used for data augmentation. Note that a description is given of an example in which each of the first data augmentation and the second data augmentation is a process of an identical type, and parameters used for the process are different from each other for simplification of the description. However, as described later as a modification, a combination of image conversion may be different between the first data augmentation and the second data augmentation.

Figure 6A:
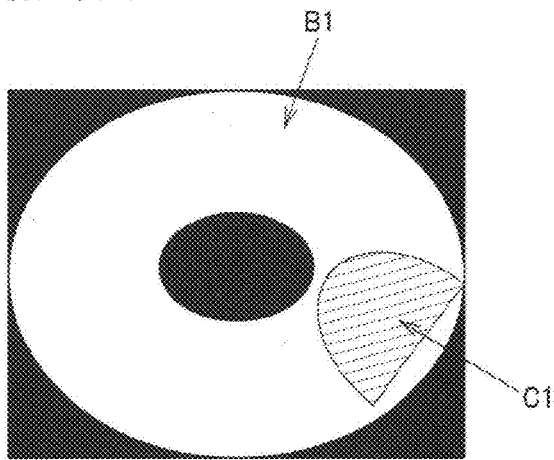
FIG. 6A is a schematic diagram illustrating an example of an input image.

FIG. 6A is a schematic diagram illustrating an example of the input image. FIG. 6A illustrates an example of the in-vivo image. B1 is a region corresponding to an inner wall of the large bowel, and C1 is a polyp region. FIG. 6B is a schematic diagram illustrating an example of the first augmented image, and FIG. 6C is a schematic diagram illustrating an example of the second augmented image. Similarly in FIGS. 6B and 6C, B2 and B3 each correspond to the inner wall of the large bowel, and C2 and C3 each correspond to the polyp region. In these drawings, the image conversion performed in each of the first data augmentation and the second data augmentation is the brightness correction process. In a case where $\gamma$ in the first data augmentation is $\gamma 1$ and $\gamma$ in the second data augmentation is $\gamma 2$, a relation of $1 < \gamma 1 < \gamma 2$ holds. Hence, the brightness of each of the first augmented image illustrated in FIG. 6B and the second augmented image illustrated in FIG. 6C is reduced as compared with the input image, and a degree of reduction in the brightness of the second augmented image is larger than that of the first augmented image. Performing such data augmentation enables inclusion of an image darker than the input image in a target for the machine learning. This enables enhancement of accuracy in detecting a polyp whose image is captured as a dark image, and the like.

Figure 6D:
FIG. 6D illustrates a specific example of the input image.
Figure 6B:
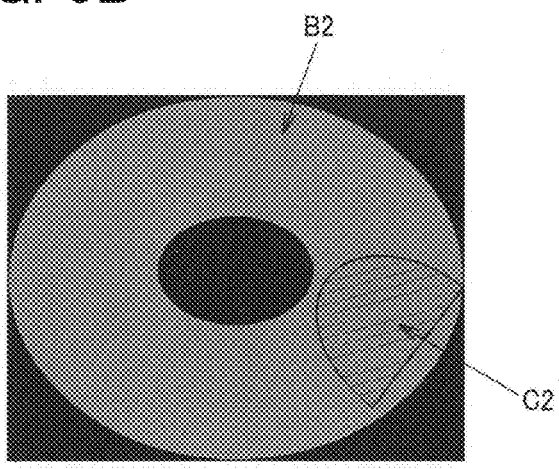
FIGS. 6B and 6C are schematic diagrams each illustrating an example of an augmented image.
Figure 6E:
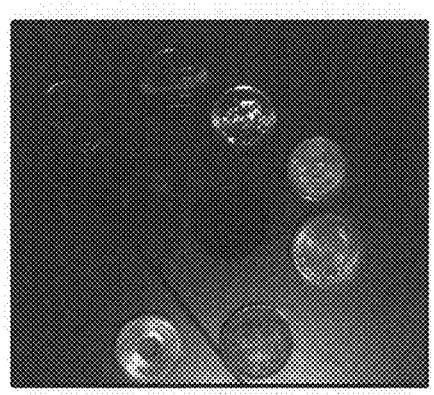
FIGS. 6E and 6F each illustrate a specific example of the augmented image.
Figure 6C:
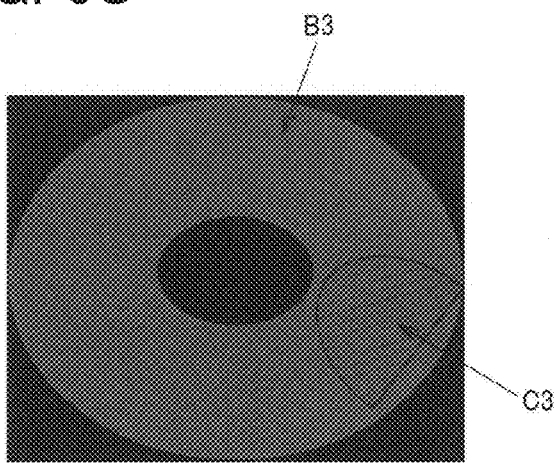
Figure 6F:
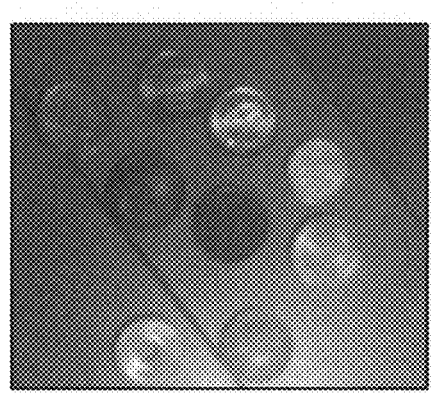

FIG. 6D illustrates an example of the input image. FIGS. 6E and 6F each illustrate an example of an augmented image based on the input image. Note that FIGS. 6D to 6F each illustrate a general image different from the in-vivo image. The image conversion in the data augmentation that generates the augmented image in FIG. 6E is the brightness correction process. In this case, $\gamma$ is larger than 1, and the brightness of the augmented image illustrated in FIG. 6E is reduced as compared with the input image. The image conversion in the data augmentation that generates the augmented image in FIG. 6F is the smoothing process. With the smoothing process, the augmented image illustrated in FIG. 6F becomes an image having an increased blurred level as compared with the input image.

The description is now back to the flowchart illustrated in FIG. 4. In step S106, the neural network application section 33 generates the first output by inputting the first augmented image to the neural network. In step S106, the neural network application section 33 also generates the second output by inputting the second augmented image to the neural network. Note that in a case where a process in step S106 is performed for the first time, a weight coefficient of the neural network is the value initialized in step S101. In a case where the process in step S106 is performed for the second time or later, the weight coefficient is a value updated by a process in step S110, which will be described later.

Figure 7:
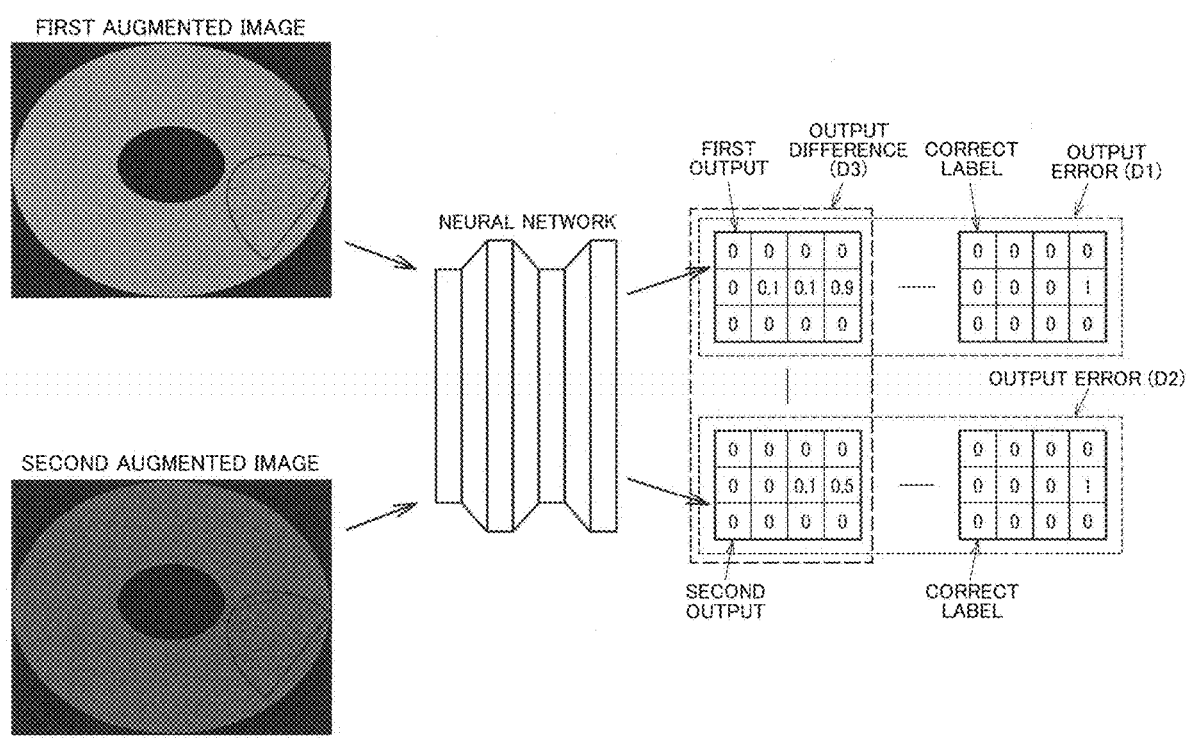
FIG. 7 is a diagram for describing a process of obtaining an output error and an output difference.

FIG. 7 is a diagram for describing a process of applying the neural network, and a process of calculating the overall error, which will be described later. As illustrated in FIG. 7, the present embodiment acquires the first output and the second output by inputting the first augmented image and the second augmented image to the neural network. In the example in FIG. 7, the first output is information, with respect to each of 4×3 regions, that is brought into correspondence with probability data indicating a probability that the region is a polyp. In this example, the number of elements is 4×3 for simplification of the description, but output data may include, for example, elements corresponding to the number of pixels of the input image. The same applies to the second output. Subsequently, in step S107, the output error calculation section 37 calculates the output error of the neural network based on at least one of the first output or the second output, and the correct label acquired by the acquisition section 20. The correct label is information, with respect to each of 4×3 regions as illustrated in FIG. 7, that is brought into correspondence with 1 in a case where the region is a polyp, and that is brought into correspondence with 0 in a case where the region is not a polyp. Specifically, the correct label is information including the number of elements identical to that of the output data. Note that the correct label is, for example, a correct label itself that is brought into correspondence with the input image. However, in the case where the object detection process is performed and the affine transformation is performed as the data augmentation, the affine transformation changes a position and size of the detection target such as a polyp. To address this, in the case of performing the data augmentation including the affine transformation in the object detection process, it is preferable to correct the correct label at the time of performing the affine transformation. Alternatively, the affine transformation may be omitted from the data augmentation in the case of performing the object detection process.

The output error is information (D1) indicating an error between the first output and the correct label, information (D2) indicating an error between the second output and the correct label, or information indicating both thereof. The output error may be sigmoid cross entropy, or may be softmax cross entropy. These output errors are preferable in the case of performing the image classification process and the object detection process. For example, the sigmoid cross entropy is used in a case of performing binary classification, and the softmax cross entropy is used in a case of performing multi-class classification. Alternatively, the output error may be a square error or the like. The square error or the like is preferable when utilizing the neural network for the image conversion process. However, a relationship between the process using the neural network and the output error is not limited to those described above, and output errors in various manners can be applied as the output error in accordance with the present embodiment.

Subsequently, in step S108, the output difference calculation section 35 calculates the output difference that is the degree of difference between the first output and the second output. The output difference is numeric value information whose value becomes larger as the difference between the first output and the second output becomes larger. The output difference calculation section 35 obtains the output difference based on a square error calculated for each element of the first output and second output. For example, the output difference is a sum of square errors of respective elements. Alternatively, the output difference calculation section 35 may obtain the output difference based on a Huber error calculated for each element of the first output and the second output. For example, the output difference is a sum of Huber errors of respective elements. The Huber error can be obtained by the following Expression (4). In the Expression (4), a represents the first output, and b represents the second output. Using the Huber error can reduce influence of outliers. Alternatively, the output difference calculation section 35 may obtain the output difference based on a cross-correlation between the first output and the second output. The output difference is, for example, a reciprocal of a cross-correlation function. In a case of the example illustrated in FIG. 7, each of the first output and the second output is two-dimensional array data, and a method of obtaining the cross-correlation function between two two-dimensional arrays is widely known. Applying such a method enables calculation of the cross-correlation function between the first output and the second output. With the usage of the reciprocal of the cross-correlation function, a relevance among elements included in the outputs can be taken into consideration. In addition, the output difference calculation section 35 may use Kullback-Leibler divergence between probability distribution of the first output and probability distribution of the second output as the output difference. That is, the output difference calculation section 35 may use a distance between the probability distribution of the first output and the probability distribution of the second output as the output difference.

Expression 4

$$huberloss(a, b) = \begin{cases} \frac{1}{2}(a-b)^2 & (|a-b| < 1) \\ |a-b| - \frac{1}{2} & (\text{otherwise}) \end{cases} \quad (4)$$

As described above, the method in accordance with the present embodiment enables obtaining of the information indicating the degree of difference between the first output and the second output as the output difference, and various kinds of methods can be applied at this time.

Subsequently, in step S109, the weight coefficient updating section 39 calculates the overall error including the output difference, and calculates an error in each layer of the neural network based on the overall error. A process in step S109 corresponds to a process of obtaining a change amount of the overall error at the time of changing the weight coefficient of each layer, that is, a gradient (partial differential). Note that a backpropagation method is known as a method of efficiently obtaining the gradient and can also be used in the present embodiment. However, the gradient may be obtained by a method other than the backpropagation method.

Specifically, the weight coefficient updating section 39 obtains a weighted sum of the output error and the output difference. As described above, the output error is calculated based on at least one of the first output or the second output, and the correct label. For example, in a case where an error (D1) between the first output and the correct label is the output error, the overall error is a weighted sum of the output error (D1) and the output difference (D3). Each of a weight of the output difference and a weight of the output error is ½. However, the weight is not limited thereto and can be modified in various manners. Alternatively, the overall error may be a weighted sum of an error (D2) between the second output and the correct label, and the output difference (D3). Still alternatively, the overall error may be a weighted sum of three of D1 to D3.

In step S110, the weight coefficient updating section 39 then updates the weight coefficient of each layer of the neural network so as to reduce the overall error. For example, the weight coefficient updating section 39 multiplies the gradient of the weight coefficient by a training rate p and subtracts a result of multiplication from a current value of the weight coefficient.

In the conventional method, the overall error is obtained from the output error. Thus, the conventional method enables training to make an output when an image is input approximate to the correct label, but does not take into consideration of a relationship between augmented images. In the present embodiment, on the other hand, the weighted sum of the output error and the output difference is the overall error. Hence, in addition to the training in a direction of reducing the output error, that is, the training to make the output when the image is input approximate to the correct label, the present embodiment enables training in a direction of reducing the output difference. That is, performed is such training as to, when the two augmented images generated by applying the two different types of data augmentation to the identical input image are input to the neural network, make the degree of difference between the outputs corresponding to the respective augmented images approximate to zero. This can reduce variations in outputs corresponding to variations in the input image, such as a shade of color, brightness, and a smoothing level. As a result, even in a case where the variations in the application image exceed an amount of variations in the data augmentation, the present embodiment can prevent reduction in accuracy in the image processing using the trained model. A specific example is as described above with reference to A1 in FIG. 1.

Note that after the process in step S110, the processing section 30 determines whether or not an end condition has been satisfied in step S111. The end condition is, for example, that the number of times of updating the weight coefficient has reached a predetermined number of times. In a case where the stopping criteria has not been satisfied (NO in S111), the processing section 30 goes back to step S102, and repeats the processes from steps S102 to S110 described above. For example, the processing section 30 selects a new input image from a plurality of input images, and executes the processes described above using the selected input image as a target. In a case where the end condition has been satisfied (YES in S111), the processing section 30 ends the training of the neural network. Note that the processing section 30 may input a set of test images to which the correct label is attached to the neural network, and determine that the end condition has been satisfied in a case where a correct rate exceeds a given threshold.

4. Modifications in Training Processing

Some modifications in the training processing is described below.

4.1 The Number of Augmented Images Generated from One Input Image

Figure 8:
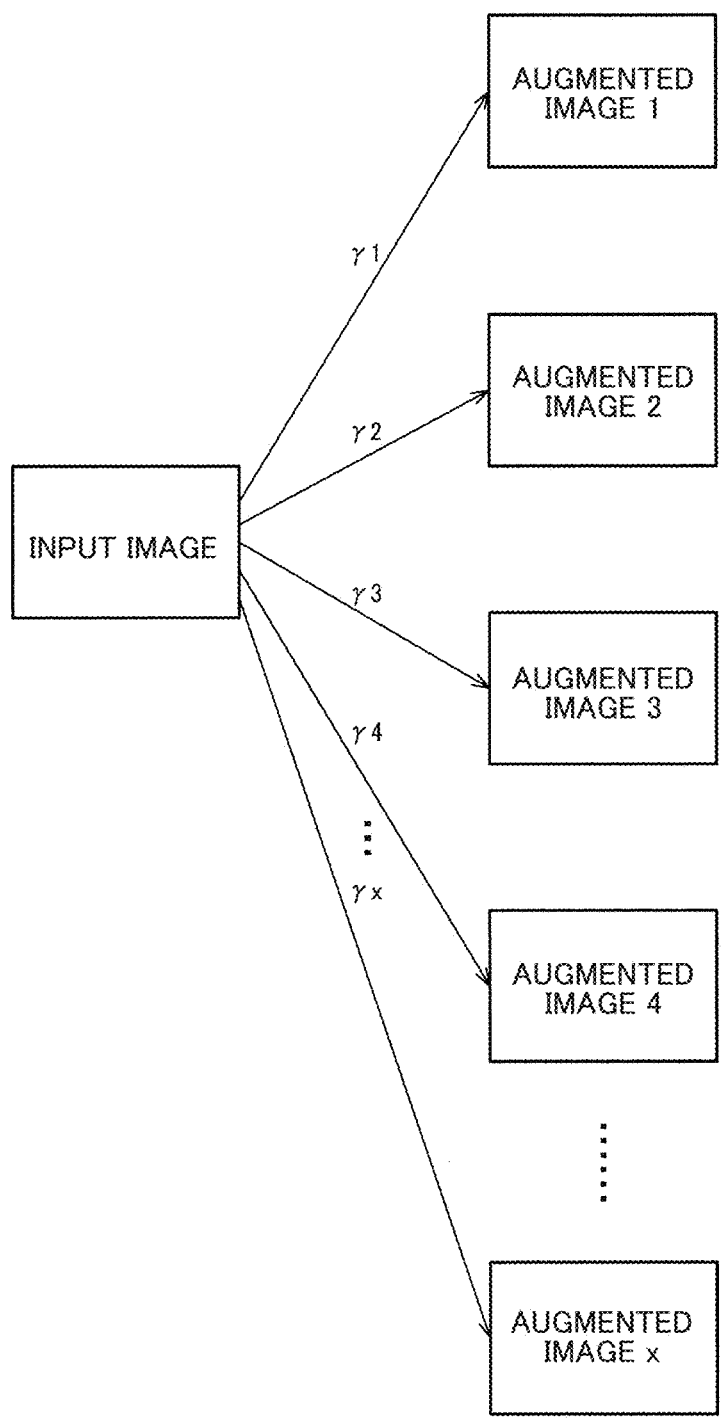
FIG. 8 illustrates an example of data augmentation with respect to one sheet of the input image.

FIG. 8 is a diagram for describing the data augmentation based on one input image. For example, in the case where the brightness correction process is performed as the data augmentation, x augmented images are generated by using x possible γs having different values as illustrated in FIG. 8. Then, x mentioned herein is an integer of two or more, and may be three or more. In this case, two out of the x augmented images are selected as the first augmented image and the second augmented image.

The number of sets of the first augmented image and the second augmented image output based on one input image is not limited to one. For example, a plurality of sets of the first augmented image and the second augmented image may be output based on the one input image so that an augmented image 1 and an augmented image 2 serve as a first set and an augmented image 3 and an augmented image 3 serve as a second set, as illustrated in FIG. 8, and the processes described above may be performed with respect to each set. In a case where the x augmented images are generated, a maximum of x(x−1)/2 sets of the first augmented image and the second augmented image can be output.

In addition, an input image that serves as a generation source of an augmented image can be utilized in the machine learning. For example, either the first augmented image or the second augmented image may be changed to the input image. In this case, the configuration enables training to reduce a degree of difference between outputs when the input image and the augmented image is input to the neural network. Hence, similarly to the case where the degree of difference between outputs of the two augmented images serves as the output difference, the configuration can prevent reduction in accuracy due to variations in the image. In this case, the first augmented image and the second augmented image are selected from a total of x+1 images including the input image and the x augmented images based on the input image. That is, a maximum of x(x+1)/2 sets of the first augmented image and the second augmented image can be output based on the one input image.

Note that the description has been given of the example of sequentially generating the first augmented image and the second augmented image when performing the processes in steps S102 to S110 one time. However, the processes of generating the augmented images may be collectively performed. For example, the processing section 30 preliminarily performs a process of generating the x augmented images from the one input image, and then accumulates an augmented image set composed of the plurality of generated, augmented images in the storage section. In this case, the processes in steps S102 to S105 can be replaced with a process of selecting appropriate two images as the first augmented image and the second augmented image from the augmented image set stored in the storage section. In addition, the processing section 30 can also collectively perform a process of obtaining the x augmented images with respect to each of a plurality of input images. Furthermore, the flow of the processing in accordance with the present embodiment is not limited to that illustrated in FIG. 4, and can be modified in various manners.

4.2 Another Example of First Data Augmentation and Second Data Augmentation

The description has been given of the example in which the data augmentation is the brightness correction process, with reference to FIGS. 6A to 6C, and FIG. 8. However, the data augmentation on the input image may be a combination of two or more processes.

Figure 9:
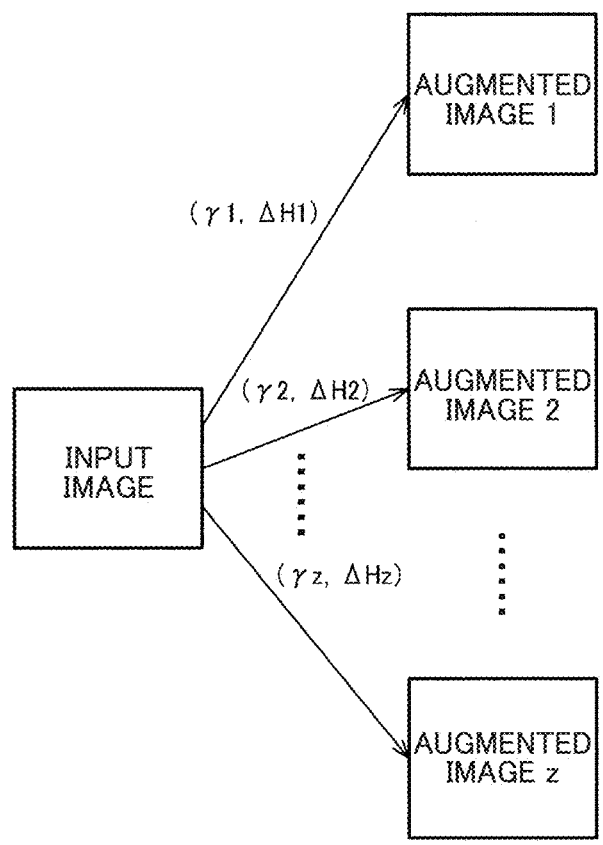
FIG. 9 illustrates another example of data augmentation with respect to one sheet of the input image.

FIG. 9 is a diagram for describing another example of the data augmentation. The data augmentation section 31 performs the gamma correction process on the input image using γ1 to γz as parameters, and the color correction process using ΔH1 to ΔHz as parameters, where z is an integer of two or more. Focusing on given augmented images i and j, since the necessity of generating a plurality of identical augmented images is low, a parameter is set to satisfy at least one of γi≠γj or ΔHi≠ΔHj, where each of i and j is an integer that is equal to or larger than 1 and equal to or smaller than z, and that satisfies i≠j.

The data augmentation section 31 outputs two out of the augmented images 1 to z as the first augmented image and the second augmented image. In this case, each of the first augmented image and the second augmented image is obtained by an identical combination of two processes, and at least one of two parameters corresponding to the two processes is different from each other. In this case, although there is a possibility that variations both in brightness and shade of color occur in the first augmented image and the second augmented image, the method in accordance with the present embodiment can reduce output variations of the neural network due to the variations.

In addition, since the necessity of generating an augmented image that is matched with the input image is low in the data augmentation, a parameter is set to satisfy at least one of γi≠1 or ΔHi≠0. In other words, in a case of ΔHi≠0, γi=1 may be permitted. In a case of γi≠1, ΔHi=0 may be permitted. That is, in the example illustrated in FIG. 9, either the gamma correction process or the color correction process may be omitted.

In this case, the augmented images 1 to z are any of an image on which only the brightness correction process is performed, an image on which only the color correction process is performed, and an image on which the brightness correction process and the color correction process are performed. Hence, assumed is not only a case where the first augmented image and the second augmented image are obtained by an identical combination of processes and having different parameters, but also a case where the first augmented image and the second augmented image are obtained by different combinations of processes in the first place. The combination of processes mentioned herein is information that identifies processes included in the data augmentation, and that indicates any of "only the brightness correction process,", "only the color correction process" and "the brightness correction process and the color correction process". For example, assumed is a case where the first augmented image is an image obtained by performing the brightness correction process on the input image, and the second augmented image is an image obtained by performing the color correction process on the input image.

However, as described above, "only the brightness correction process," can be considered as "the brightness correction process, and the color correction process with ΔH=0", and "only the color correction process" can be considered as "the brightness correction process with γ=1, and the color correction process". That is, a case where a combination of processes is different from each other is included in the case where a combination of two processes is identical and at least one of two parameters corresponding to the two processes is different from each other. Note that the description has been given of the two processes of the brightness correction process and the color correction process, but the data augmentation may include three or more processes as described above.

4.3 Adjustment Process in Data Augmentation Range

Figure 10:
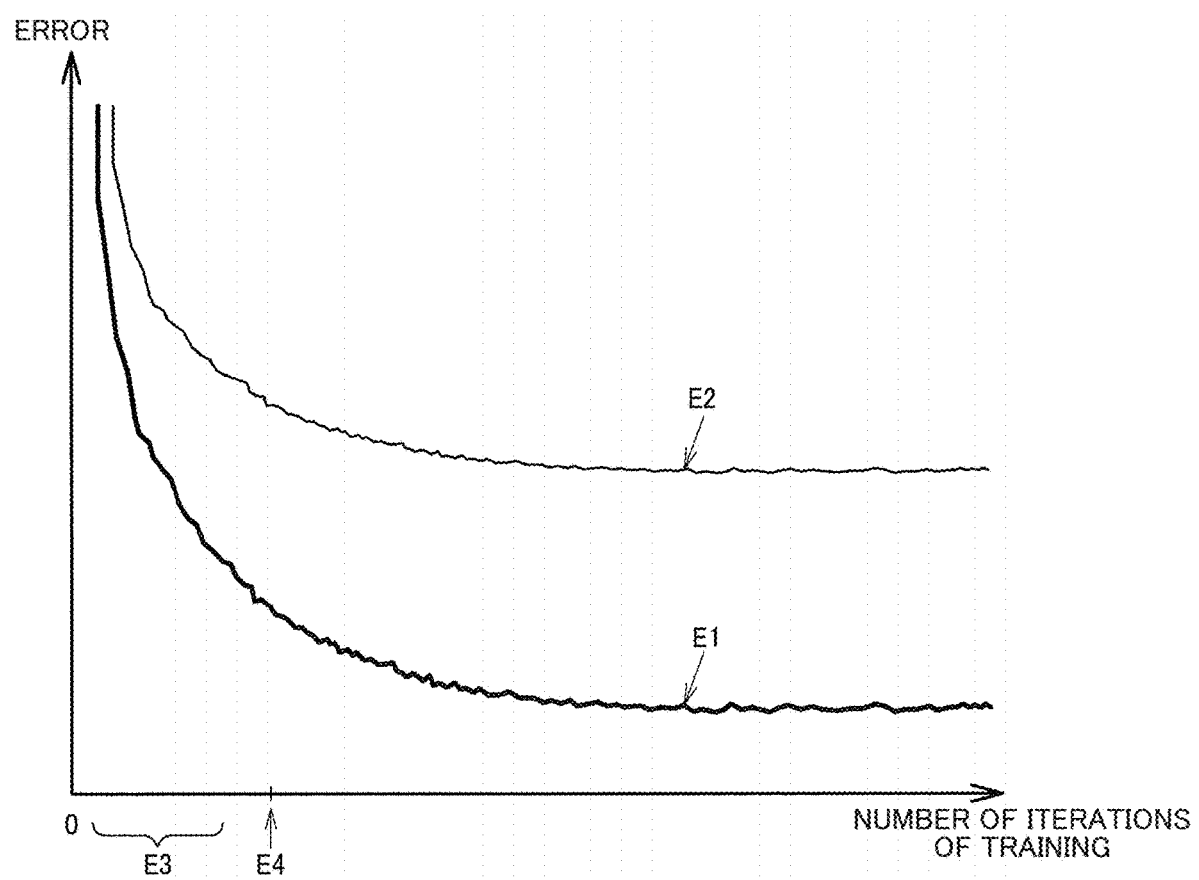
FIG. 10 is a relationship diagram between the number of iterations of training and an error.

FIG. 10 is a diagram illustrating a degree of reduction in error in a case where training is repeated. An abscissa axis in FIG. 10 represents the number of iterations of the training, and an ordinate axis represents an error. The number of iterations of the training corresponds to the number of times of updating the weight coefficient, and is, for example, the number of times of execution of step S110 in FIG. 4.

E1 in FIG. 10 represents a degree of reduction in the output error in a case of performing training so as to reduce the output error without using the output difference. In the case of the example illustrated FIG. 7, E1 corresponds to a case of performing the training processing using the overall error including the information (D1) indicating the error between the first output and the correct label and the information (D2) indicating the error between the second output and the correct label, but not including the output difference (D3).

The method in accordance with the present embodiment is different from the method indicated by E1 in that the output difference is included in the overall error. Performing the training to reduce the output difference can prevent reduction in accuracy due to variations in the application image. However, since not only the output error but also the output difference needs to be reduced, there is a possibility that the training becomes difficult. As indicated by E2, for example, in the method in accordance with the present embodiment, an error is hard to be reduced as compared with E1 not using the output difference. Specifically, there is a possibility that that an amount of reduction in error becomes small at an early stage of the training, and an error becomes large when a value converges. Note that the value converging means a state where a change amount of the error becomes sufficiently small with respect to an increase in number of iterations of the training.

Specifically, in a case where variations between the first augmented image and the second augmented image are excessively large, a degree of difference between the first output and the second output tends to be large, so that the training to make the output difference approximate to zero becomes more difficult.

To address this, in the present embodiment, a difference between a first parameter that decides the first data augmentation and a second parameter that decides the second data augmentation may be within a given range. This reduces the difference between the first augmented image and the second augmented image, and can thereby increase a degree of convergence in the training using the output difference. The increased degree of convergence in the training may indicate that an amount of reduction in error is large, that a value of the error at the time of convergence is small, or both of these cases.

For example, in a case of the first data augmentation and the second data augmentation being identical processes, a difference in parameters between these processes is set to a value equal to or smaller than a threshold. If the process is the gamma correction process, an absolute value of a difference between γ in the first data augmentation and γ in the second data augmentation is equal to or smaller than the threshold. For example, as described above, when the lower limit value and upper limit value of γ in the gamma correction process are set, the upper limit value and the lower limit value are set so that the difference between the upper limit value and the lower limit value becomes a value equal to or smaller than a gamma threshold. With this setting, even in a case where the data augmentation section 31 decides a value of γ at region within a range between the lower limit value and the upper limit value, the absolute value of the difference between γ used for generating the first augmented image and γ used for generating the second augmented image is guaranteed to be a value equal to or smaller than the gamma threshold. However, the data augmentation section 31 may first decide γ used for the first augmented image, and then decide γ used for the second augmented image so that the difference from γ used for the first augmented image becomes a value equal to or smaller than the gamma threshold. Specific processing can be modified in various manners.

In a case of the first data augmentation and the second data augmentation being a combination of two or more processes, a difference in parameters with respect to each process is set to a value equal to or smaller than a given threshold. If the processes are the gamma correction process and the color correction process, the absolute value of the difference between γ in the first data augmentation and γ in the second data augmentation becomes a value that is equal to or smaller than the given gamma threshold, and each parameter is set so that an absolute value of a difference between ΔH in the first data augmentation and ΔH in the second data augmentation becomes a value that is equal to or smaller than a given hue threshold.

Alternatively, an evaluation value indicating a difference between the first parameter and the second parameter may be calculated based on the difference in γ and the difference in ΔH. Each parameter is set so that the evaluation value becomes a value equal to or smaller than a threshold in the first data augmentation and the second data augmentation.

Note that in a case where a combination of processes in the first data augmentation and a combination of processes in the second data augmentation are different from each other, a process that is not executed is only required to be regarded as a process to be executed using a parameter that does not vary the input image, as described above. The parameter that does not vary the input image is, for example, γ=1, and ΔH=0, as described above. The smoothing level of the input image is maintained by setting the number of applying the Gaussian filter to zero in the smoothing process. The image sharpness level of the input image is maintained by setting the number of applying the edge enhancement filter to zero in the image sharpening process. In the noise addition process, a noise amount of the input image is maintained by setting impulse noise to zero, that is, setting a ratio of pixels whose pixel values are to be changed to zero. In the affine transformation process, a size, angle, and position of the input image is maintained by setting a diagonal element used in the affine transformation, out of matrix elements, to one and setting the other elements to zero.

Specifically, in a case where the output error or the overall error is set as a determination target error, a given range is set based on a degree of reduction in the determination target error as a result of the process of updating the weight coefficient. This allows a permissible difference in parameter between the first data augmentation and the second data augmentation to be decided based on a degree of progress of the training and the degree of convergence.

For example, the processing section 30 sets the given range, for example, the lower limit value and upper limit value of the parameter, to initial values. The processing section 30 performs training processing to reduce the output error including the output difference and the output error, and determines a degree of reduction in the determination target error. In a case of determining that the determination target error is sufficiently reduced, the processing section 30 determines that the lower limit value and the upper limit value are appropriate. In a case where the degree of reduction in error is small, the processing section 30 determines that the training becomes difficult due to the given range being too wide. The processing section 30 thus updates the given range to become narrower. For example, the processing section 30 performs at least one of a process of increasing the lower limit value or a process of decreasing the lower limit value. Note that in a case where the data augmentation is a combination of a plurality of processes, the processing section 30 may update the upper limit value or lower limit value of a parameter in all of the processes, or may update the upper limit value or lower limit value of a parameter in part of the processes.

Note that in a case of adjusting the given range using the degree of reduction in actual error in this manner, the processing section 30 may determine the degree of reduction in the determination target error when the end condition in step S111 is satisfied in FIG. 4. That is, the processing section 30 may determine whether or not the given range is appropriate in accordance with how much degree the determination target error is reduced when the training is completed. However, in a case where the given range is too wide, the processing section 30 needs to repeat the processes in steps S102 to S110 again after narrowing the given range. That is, when the given range is set, there is a possibility that a result of the training is discarded depending on the degree of reduction in the determination target error. As illustrated in FIG. 10, the processing section 30 can determine the degree of reduction in error from a degree of reduction in error at a training initial stage (E3), specifically, a gradient of a graph. Alternatively, even with the number of iterations denoted by E4, at which the error does not sufficiently converges, the processing section 30 can determine the degree of reduction in accordance with a magnitude of the value of the error. That is, the number of iterations at the time of determining the degree of reduction in the determination target error may be smaller than that of the end condition of the training.

In addition, the processing section 30 may determine whether the degree of reduction in the determination target error is high or low by making comparison with a fixed threshold. However, the degree of reduction in error is changed in accordance with a configuration of the neural network, images used for the training, or the like. For this reason, in a case of using the fixed threshold, there is a possibility that the processing section 30 cannot correctly determine whether or not the error is sufficiently reduced.

Hence, the processing section 30 may use information denoted by E1 illustrated in FIG. 10 as a comparison target. Specifically, the processing section 30 sets the given range based on a process of comparing a degree of reduction in the output error (E1) in a case of updating the weight coefficient in each layer of the neural network based on the output error and a degree of reduction in the determination target error (E2) in a case of updating the weight coefficient in each layer of the neural network based on the overall error including the output difference. With this process, the processing section 30 can appropriately determine how difficult the training becomes by using the output difference. Considering that the comparison target is the output error, the output error out of the overall error may be used as the determination target error. With this configuration, the comparison is made between output errors. As a result, the processing section 30 can determine whether the degree of reduction in error is high or low with high accuracy.

4.4. Data Augmentation Region

The data augmentation section 31 may set part of regions in the input image as a data augmentation region. The data augmentation section 31 generates the first augmented image by applying the first data augmentation on the data augmentation region in the input image, and generates the second augmented image by applying the second data augmentation on the data augmentation region in the input image. This enables application of data augmentation to part of the input image in a limited manner.

For example, in an in-vivo image that is captured by the endoscope apparatus, an edge region is dark and has a low contrast as compared with a central region. Thus, in a case where the object serving as the recognition target exits in the edge region of the application image, a captured image of the object becomes unclear. For example, the data augmentation section 31 sets the edge region of the image as the data augmentation region, and executes the brightness correction process that reduces brightness and the smoothing process that increases the smoothing level. This can increase accuracy in recognizing the unclear object.

Or in the in-vivo image, illumination light mirror-reflected on the object is incident on an objective lens, thereby making a bright spot likely to occur. The bright spot is a region having high luminance, and is, for example, a region in which overexposure occurs. In particular, in a case where the imaging section and the object have a correct positional relationship, the bright spot is likely to occur in the central region of the image. In this case, the data augmentation section 31 sets the central region of the image as the data augmentation region, and executes the noise addition process of adding such impulse noise as to make a pixel value a maximum value. This can increase accuracy in recognizing the object even in a case where the bright spot occurs in the image.

Note that the processing described above is merely an example, and the data augmentation in a case of setting the edge region in the image as the data augmentation region is not limited to the brightness correction process and the smoothing process. The data augmentation in a case of setting the central region of the image as the data augmentation region is not limited to the noise addition process.

In addition, the data augmentation region may be set from a different perspective. For example, in a case where a region in which an image of the target object is captured in the input image is a target region, the data augmentation region may be set based on the target region. Regardless of a manner of capturing an image, it is preferable to set the target region as the data augmentation region from a perspective of increasing accuracy in recognizing the target object. Note that the target object is an object having a relatively higher priority over another object for a user. For example, in a case where the input image is the in-vivo image and the user is a doctor who performs medical treatment, the target object is a mucous membrane section or a lesion. As described above, the target object may be a polyp. As another example, if a target that the doctor wants to observe is bubbles or feces, the target object is the bubbles or the feces. The target to which the user should pay attention is different depending on an observation purpose, but in any cases, the object having a relatively higher priority in observation over another object for the user at the time of the observation is the target object.

However, there is a case where a difference in contrast between the target region and a background region is small in the input image. Such an object is difficult to be visually detected by the user, and is preferably a target of the recognition process using the machine learning. In this case, when the data augmentation including the smoothing process is performed on the target region, a difference in contrast that has been originally small becomes further smaller. As a result, there is a possibility that training for detecting the target region becomes difficult. In a case where such a case is assumed, the data augmentation section 31 excludes the target region from a target of the data augmentation. That is, a region excluding the target region from the input image is set as the data augmentation region.

In addition, the output error calculation section 37 may calculate the output error using part of regions in the input image. For example, in a case where a region in which an image of the target object is captured in the input image is set as the target region, the output error calculation section 37 may calculate the output error in the region corresponding to the target region.

4.5 Second Neural Network

The neural network application section 33 may generate a third output by inputting the first augmented image to a second neural network that shares part of a structure of the neural network, and generate a fourth output by inputting the second augmented image to the second neural network. The neural network application section 33 outputs the third output and the fourth output to the output difference calculation section 35.

The output difference calculation section 35 calculates a second output difference indicating a degree of difference between the third output and the fourth output. The second output difference is numeric value information that becomes larger as the difference between the third output and the fourth output becomes larger. The second output difference can be calculated based on a square error, a Huber error, a cross-correlation function, or the like, similarly to the output difference described above. The output difference calculation section 35 outputs the second output difference to the weight coefficient updating section 39.

The weight coefficient updating section 39 updates a weight coefficient in each layer of the neural network based on the second output difference. Note that the output difference may be used to update the weight coefficient in each layer of the neural network. For example, the weight coefficient updating section 39 calculates an overall error based on a weighted sum of the output error, the output difference, and the second output difference, and updates the weight coefficient in each layer of the neural network so as to reduce the overall error.

Figure 11:
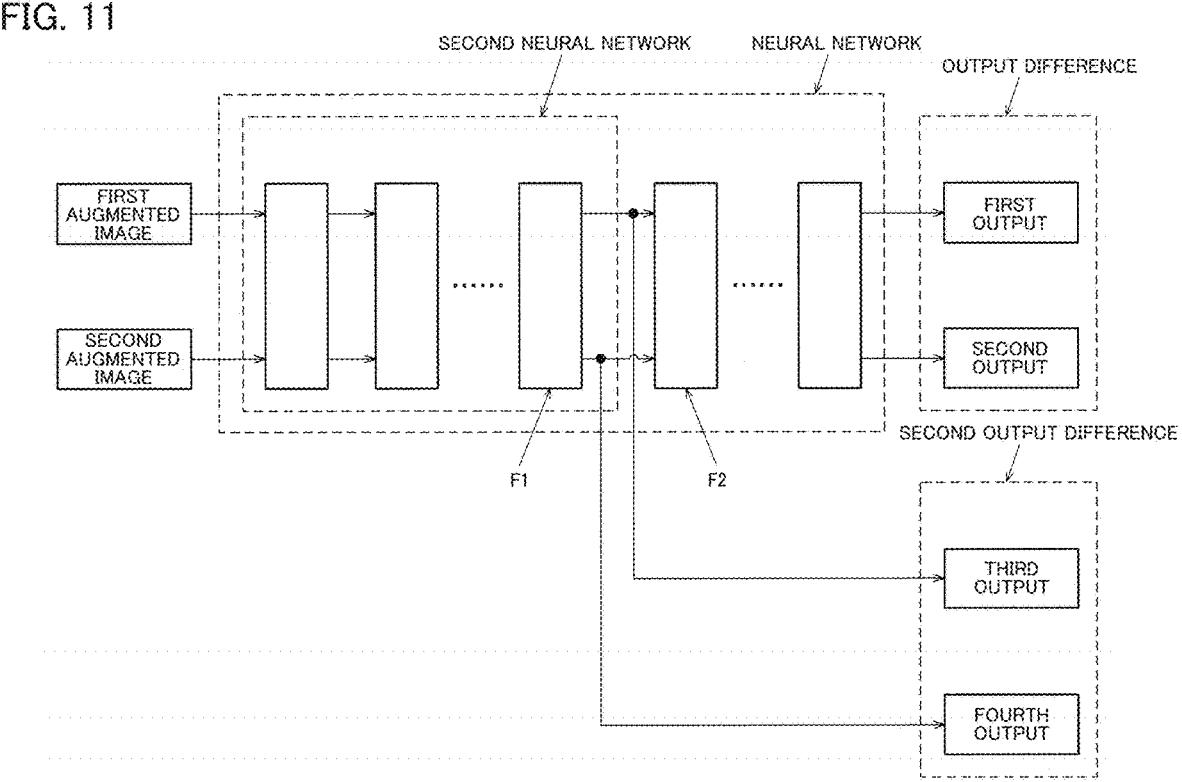
FIG. 11 illustrates a configuration example of a second neural network.

FIG. 11 is a diagram for describing the second neural network, the third output, and the fourth output. Similarly to the example described with reference to FIG. 7, the first output is generated by inputting the first augmented image to the neural network, and the second output is generated by inputting the second augmented image to the neural network. The output difference is obtained based on the first output and the second output. Note that each rectangle included in the neural network represents one layer in the neural network, and may be a convolution layer, a pooling layer, or a layer other than these layers.

The second neural network in the present embodiment, for example, corresponds to the input layer of the neural network to a given intermediate layer (F1), as illustrated in FIG. 11. In a case where the first augmented image is input, an output of the intermediate layer denoted by F1 is input to the next layer (F2), and also output to the output difference calculation section 35 as the third output. Similarly, in a case where the second augmented image is input, an output of the intermediate layer denoted by F1 is input to the next layer (F2), and also output to the output difference calculation section 35 as the fourth output.

This enables training so as to reduce the difference between the first output and the second output and also reduce the difference between the third output and the fourth output. The second output difference contributes to reduction in error in F1 and layers in a former stage. Since not only variations in outputs from the neural network but variations in the intermediate layer are prevented, the present embodiment can build the neural network that has higher resistance to image variations.

While the description has been given of the example of using an output from the intermediate layer denoted by F1 as the third output or the fourth output without any change in FIG. 11, the configuration of the neural network is not limited thereto.

Figure 12:
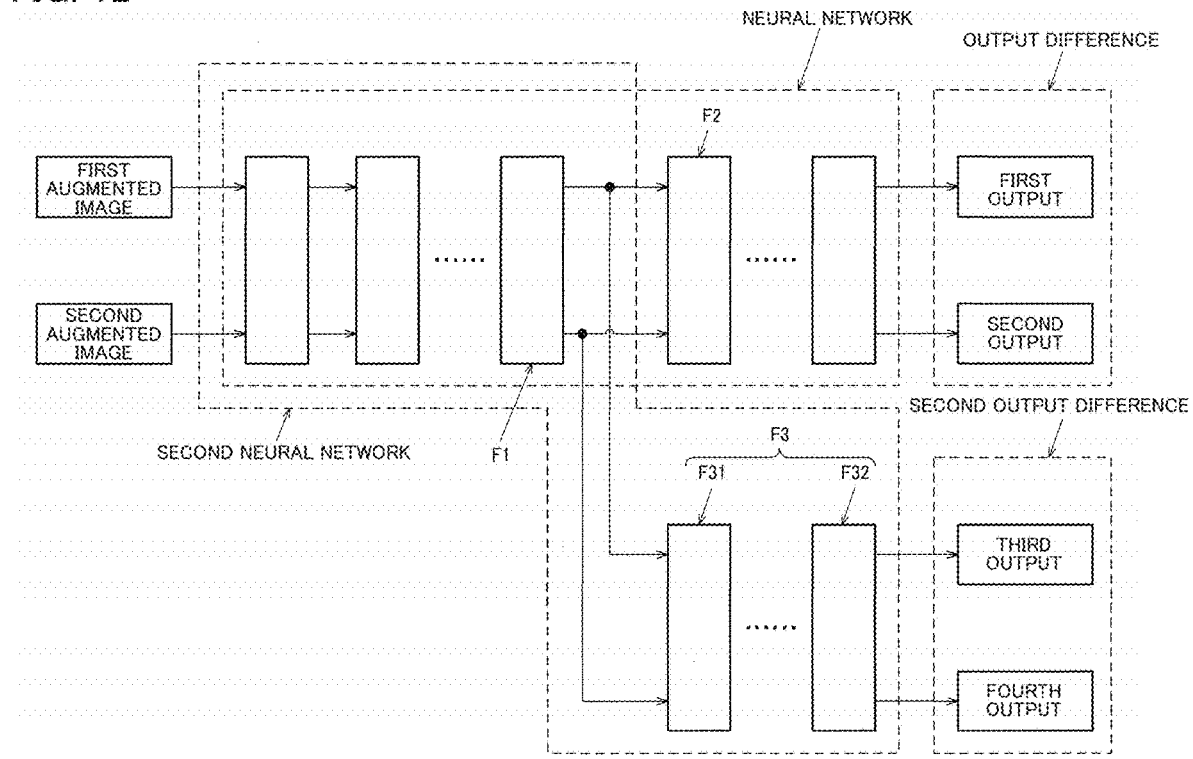
FIG. 12 illustrates another configuration example of the second neural network.

FIG. 12 is another diagram for describing the second neural network, the third output, and the fourth output. For example, the second neural network may include the input layer of the neural network to the given intermediate layer (F1) and be composed of a layer (F3) that is not included in the neural network. In an example illustrated in FIG. 12, the output from the intermediate layer denoted by F1 is input to a layer denoted by F31. The third output or the fourth output is output from an output layer denoted by F32 after undergoing processing in each layer denoted by F3. While the description has been given of a case where F3 includes a plurality of layers, F3 may be one layer.

Also in the example illustrated in FIG. 12, variations in the intermediate layer are prevented, so that the present embodiment can build the neural network that has higher resistance to image variations. In addition, F1 is the intermediate layer in FIG. 12, but may be changed to the output layer. That is, the third output and the fourth output may be output by inputting the first output and the second output to one or the plurality of layers denoted by F3.

5. Image Processing Device Serving as Inference Device

The description has been given of the image processing method of performing the training processing based on the output difference, and the training device 10. The method in accordance with the present embodiment can be applied to an image processing method of acquiring an application image, generating an output by inputting the application image to the neural network, and performing a recognition process targeting the application image based on the output. While the recognition process is exemplified herein, image processing on the application image may be an image conversion process. Alternatively, the method in accordance with the present embodiment can be applied to the image processing device 40 that performs processing on the application image based on a training result.

Figure 13:
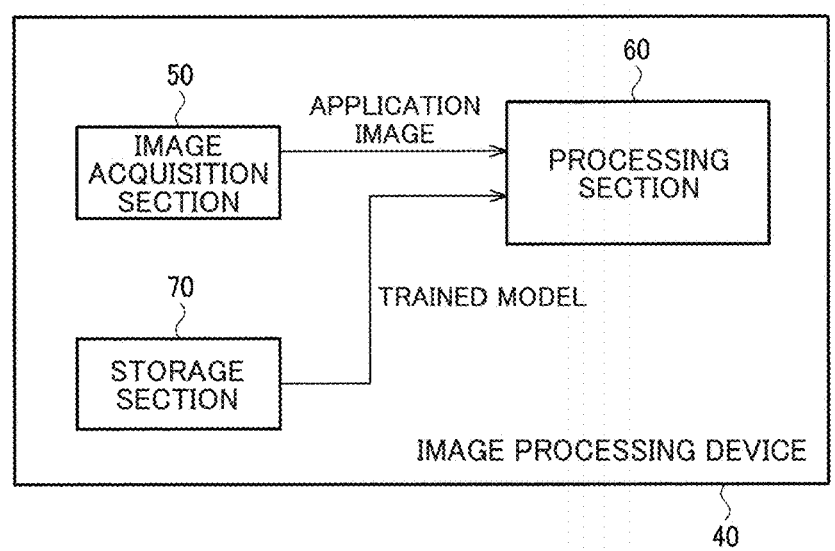
FIG. 13 illustrates a configuration example of an image processing device.

FIG. 13 illustrates a configuration example of the image processing device 40. The image processing device 40 includes an image acquisition section 50, a processing section 60, and a storage section 70. The image acquisition section 50 acquires the application image. The storage section 70 stores the trained model generated by the training device 10. The trained model is utilized as a program module, which is part of artificial intelligence software.

The processing section 60 performs an inference process on the application image based on the trained model. The inference process mentioned herein corresponds to the image processing on the application image, and may be the recognition process such as the image classification process and the object detection process, or may be the image conversion process on the application image. The processing section 60 operates to output a result of the image processing on the application image serving as an input, in accordance with an instruction from the trained model stored in the storage section 70.

The processing section 60 is implemented by various kinds of software and a processor, similarly to the processing section 30 of the training device 10. The storage section 70 may be a semiconductor memory, a register, a magnetic storage device, or an optical storage device. Note that the processing section 60 may include dedicated hardware for performing processing based on the trained model. In the case of the example of using the neural network, the processing section 60 may include a circuit device that performs a filter process in convolution calculation and a sum-of-product calculation process in the fully connected layer. The circuit device can be implemented by, for example, a field-programmable gate array (FPGA) or the like. In this case, the storage section 70 stores a weight coefficient as the trained model, and the processing section 60 including the circuit device operates in accordance with the weight coefficient to perform the recognition process or the like. Alternatively, the storage section 70 may store both a program for performing the filter process or the sum-of-product calculation process and the weight coefficient as the trained model. In this manner, the specific configuration in which the processing section 60 operates in accordance with an instruction from the trained model stored in the storage section 70 can be modified in various manners.

The image processing device 40 may be one device, or may include a plurality of devices. For example, the image processing device 40 may be implemented by a terminal device such as a personal computer (PC) and a server system operating in cooperation. In addition, the storage section 70 may be a read-only memory (ROM) or a random-access memory (RAM). Specifically, the trained model written in the storage section 70 may be non-rewritable or rewritable. In a case where the trained model is rewritable, for example, information of the trained model is aggregated in the server system, and the storage section 70 of the image processing device 40 stores the trained model acquired from the server system. In this case, since the trained model can be managed on the server system side, the updating process or the like becomes easier.

The trained model stored in the storage section 70 is trained by generating the first augmented image by applying the first data augmentation on the input image, generating the second augmented image by applying, on the input image, the second data augmentation different from the first data augmentation, generating the first output by inputting the first augmented image to the neural network, generating the second output by inputting the second augmented image to the neural network, calculating the output difference indicating the degree of difference between the first output and the second output, and updating the weight coefficient of each layer of the neural network based on the output difference. More specifically, the trained model is a model trained by executing each step described with reference to FIG. 4.

This enables execution of the image processing on the application image using the trained model trained so as to reduce the output difference. Even if variations in hue or lightness occur in the application image and the variations exceed an amount of variations of the input image in the data augmentation, the present embodiment can prevent reduction in accuracy of the image processing.

Furthermore, a program implementing the processing performed by the image processing device 40 in accordance with the present embodiment can be stored, for example, in an information storage device, which is a computer-readable information storage medium. The program mentioned herein includes the trained model. The information storage device can be implemented by, for example, an optical disk, a memory card, a hard disk drive (HDD), a semiconductor memory, or the like. The processing section 60 performs various kinds of processing including the process of detecting the recognition target based on the program stored in the information storage device. That is, the information storage device stores the program causing a computer to function as the image processing device 40. The computer is a device including an input device, a processing section, a storage section, and an output section. The program is a program for causing the computer to execute the processing of the image processing device 40, especially the processing of the processing section 60.

Figure 14:
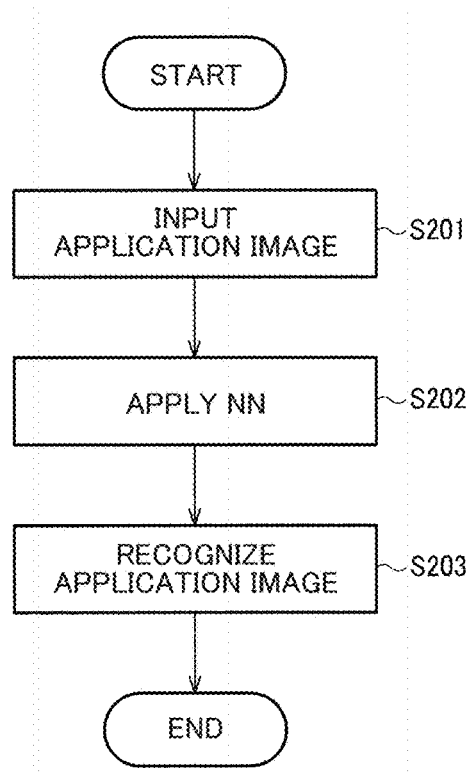
FIG. 14 is a flowchart describing an inference process using a trained model.

FIG. 14 is a flowchart describing processing in the image processing device 40. When this processing is started, in step S201, the image acquisition section 50 first acquires the application image.

Subsequently, in step S202, the processing section 60 inputs the application image to the neural network serving as the trained model to generate an output. The processing in step S202 is the convolution calculation in accordance with the set weight coefficient or the like, similarly to step S106 in FIG. 4.

In step S203, the processing section 60 executes the recognition process based on the output generated in step S202. A recognition result in step S203 may be information that identifies a category of the object whose image is captured ad described above, or may be information that can also identify a position of the object.

Note that the processing section 60 may acquire an in-vivo image captured by the endoscope apparatus as the application image and input the in-vivo image to the trained model to perform the recognition process targeting the in-vivo image. The recognition target is the target object whose image is captured in the in-vivo image. The target object is, as described above, an object having a higher priority in observation over another object for the user. This enables increased accuracy in recognizing the target object serving as the recognition target in observation of the in-vivo image. In this case, the image processing device 40 may be included in the endoscope apparatus that captures the in-vivo image.

Figure 15:
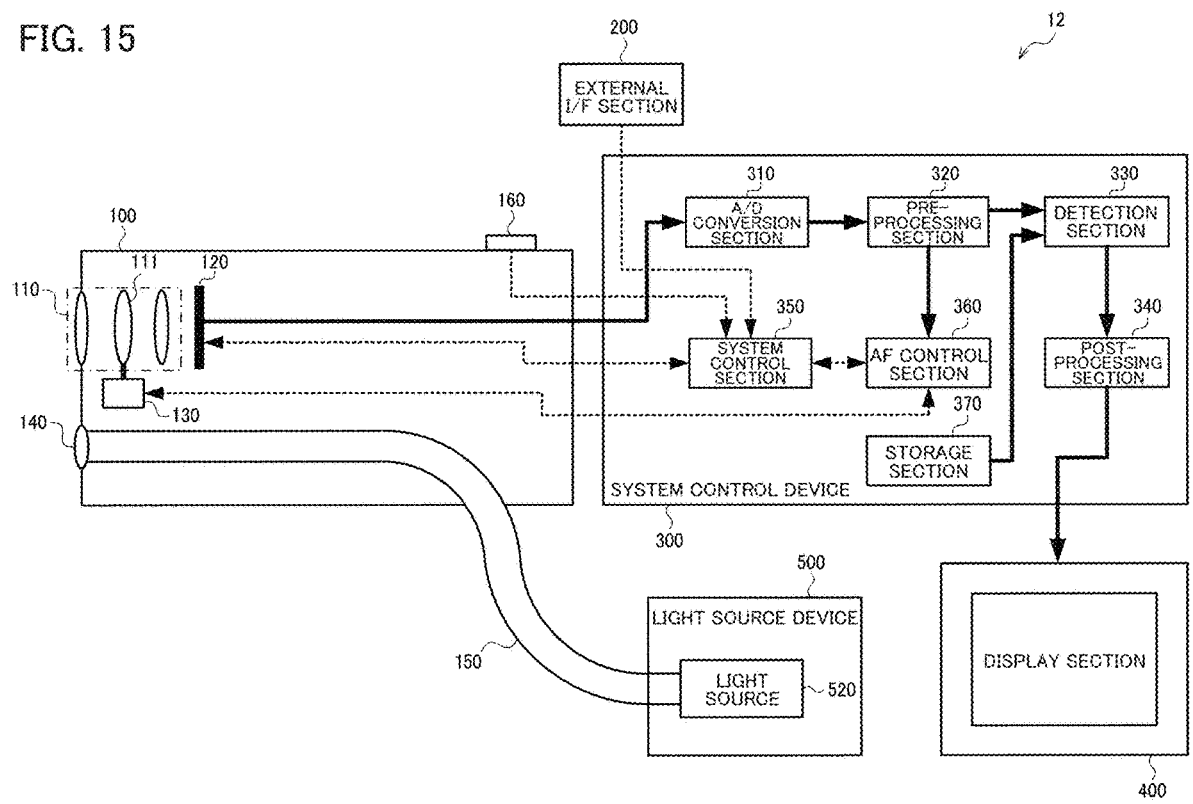
FIG. 15 illustrates a configuration example of an endoscope apparatus.

FIG. 15 is configuration example of an endoscope apparatus 12. The endoscope apparatus 12 includes an insertion section 100, an external interface (I/F) section 200, a system control device 300, a display section 400, and a light source device 500.

The insertion section 100 is a part inserted into the body. The insertion section 100 includes an objective optical system 110, an image sensor 120, an actuator 130, an illumination lens 140, a light guide 150, an Auto Focus (AF) start/end button 160.

The light guide 150 guides light emitted from a light source 520 to a distal end of the insertion section 100. The illumination lens 140 emits illumination light guided by the light guide 150 to the object. The objective optical system 110 receives the reflected light from the object and forms an image as an object image. The objective optical system 110 includes a focus lens 111, and a position of formation of the object image can be changed in accordance with a position of the focus lens 111. The actuator 130 drives the focus lens 111 based on an instruction from an AF control section 360. Note that AF is not essential, and the endoscope apparatus 12 may have a configuration of not including the AF control section 360.

The image sensor 120 receives light from the object via the objective optical system 110. The image sensor 120 may be a monochrome sensor, or a sensor including a color filter. The color filter may be a well-known Bayer filter, a complementary color filter, or another filter. The complementary color filter is a filter including filters of cyan, magenta, and yellow.

The AF start/end button 160 is an operation interface by which a user operates start/end of AF. The external I/F section 200 is an interface by which the user performs an input operation to the endoscope apparatus 12. The external I/F section 200 includes, for example, an AF control mode setting button, an AF region setting button, an image processing parameter adjustment button, and the like.

The system control device 300 performs image processing and control of the whole of the system. The system control device 300 includes an analog/digital (A/D) conversion section 310, a pre-processing section 320, a detection section 330, a post-processing section 340, a system control section 350, an AF control section 360, and a storage section 370. The system control device 300 includes, for example, the image processing device 40 illustrated in FIG. 13. Note that the A/D conversion section 310 corresponds to the image acquisition section 50 illustrated in FIG. 13. The storage section 370 corresponds to the storage section 70 illustrated in FIG. 13. The pre-processing section 320, the detection section 330, the post-processing section 340, and the like correspond to the processing section 60 in FIG. 13.

While the image sensor 120 sequentially outputs analog signals to the A/D conversion section 310, the A/D conversion section 310 converts the analog signals into digital images and sequentially outputs the digital images to the pre-processing section 320. The pre-processing section 320 performs various kinds of correction processes on captured images sequentially output from the A/D conversion section 310, and sequentially outputs the resultant images to the detection section 330 and the AF control section 360. Examples of the correction process include a white balance process, a noise reduction process, and the like.

The detection section 330 operates in accordance with the trained model stored in the storage section 370 to perform the recognition process for the target object from the captured image serving as the application image. In the case where the trained model is the neural network, the detection section 330 performs a forward direction calculation process using the weight coefficient decided by the training on the application image serving as the input. The detection section 330 outputs a result of the recognition process based on an output from the output layer.

The post-processing section 340 performs a post-process based on a result of the detection process in the detection section 330, and outputs a post-processed image to the display section 400. As the post-process mentioned herein, various processes, such as highlighting of the recognition target in the application image and addition of information indicating a detection result, can be assumed.

The system control section 350 is connected to each of the image sensor 120, the AF start/end button 160, the external I/F section 200, and the AF control section 360, and controls each section. Specifically, the system control section 350 inputs/outputs various kinds of control signals. The AF control section 360 performs AF control using application images sequentially output form the pre-processing section 320.

The display section 400 sequentially displays images output from the post-processing section 340. The display section 400 is, for example, a liquid crystal display, an electroluminescence (EL) display or the like. The light source device 500 includes the light source 520 that emits illumination light. The light source 520 may be a xenon light source, a light emitting diode (LED), or a laser light source. The light source 520 may be another light source, and a light emission method is not specifically limited.

Note that the image processing device 40 is not limited to the one included in the endoscope apparatus 12. For example, the image processing device 40 may be a PC, a server system, or the like that is arranged separately from the endoscope apparatus 12 and that can communicate with the endoscope apparatus 12.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An image processing method comprising:
generating a first augmented image by applying first data augmentation on an input image;
generating a second augmented image by applying, on the input image, second data augmentation different from the first data augmentation;
generating a first output by inputting the first augmented image to a neural network;
generating a second output by inputting the second augmented image to the neural network;
calculating an output difference indicating a degree of difference between the first output and the second output; and
updating a weight coefficient of each layer of the neural network based on the output difference.

2. The image processing method as defined in claim 1, further comprising:
acquiring a correct label corresponding to the input image
calculating an output error based on at least one of the first output or the second output, and the correct label;
determining, as an overall error, a weighted sum of the output error and the output difference; and updating the weight coefficient of each layer of the neural network based on the overall error.

3. The image processing method as defined in claim 2, the weight coefficient of each layer of the neural network being updated in such a way as to reduce the overall error.

4. The image processing method as defined in claim 2, a difference between a first parameter that decides the first data augmentation and a second parameter that decides the second data augmentation being within a given range.

5. The image processing method as defined in claim 4, in a case where the output error or the overall error is a determination target error, the given range being set based on a degree of reduction in the determination target error by an updating process of the weight coefficient.

6. The image processing method as defined in claim 5, the given range being set based on a process of making comparison between a degree of reduction in the output error in a case of updating the weight coefficient of each layer of the neural network based on the output error and the degree of reduction in the determination target error in a case of updating the weight coefficient of each layer of the neural network based on the overall error.

7. The image processing method as defined in claim 1, the output difference being determined based on a square error that is calculated with respect to each element of the first output and second output, or a Huber error that is calculated with respect to each element of the first output and second output, or a cross-correlation between the first output and the second output.

8. The image processing method as defined in claim 1, the first data augmentation including at least one of a color correction process, a brightness correction process, a smoothing process, an image sharpening process, a noise addition process, or an affine transformation process, and
the second data augmentation including at least one of the color correction process, the brightness correction process, the smoothing process, the image sharpening process, the noise addition process, or the affine transformation process.

9. The image processing method as defined in claim 1, further comprising:
setting a partial region in the input image as a data augmentation region;
generating the first augmented image by applying the first data augmentation on the data augmentation region in the input image; and
generating the second augmented image by applying the second data augmentation on the data augmentation region in the input image.

10. The image processing method as defined in claim 9, in a case where a region of a captured image of a target object is a target region in the input image, the data augmentation region being set based the target region.

11. The image processing method as defined in claim 1, the neural network being a convolutional neural network (CNN).

12. The image processing method as defined in claim 1, further comprising:
inputting an application image;
generating an application output by inputting the application image to the neural network; and
performing a recognition process targeting the application image based on the application output.

13. The image processing method as defined in claim 1, further comprising:
generating a third output by inputting the first augmented image to a second neural network that shares part of a structure of the neural network;
generating a fourth output by inputting the second augmented image to the second neural network;
calculating a second output difference indicating a degree of difference between the third output and the fourth output; and
updating a weight coefficient of each layer of the neural network based on the second output difference.

14. An image processing method using a neural network, the neural network being trained using an error including a degree of difference between a plurality of outputs corresponding to a plurality of augmented images when the plurality of augmented images is input to the neural network, the plurality of augmented images being generated by application of a plurality of types of different data augmentation to one input image,
the method comprising:
generating a first application output by inputting a first application image to the neural network;
generating a first recognition result based on the first application output;
generating a second application output by inputting a second application image to the neural network; and
generating a second recognition result based on the second application output,
in a case where the first application image and the second application image correspond to a captured image of an object and a difference between the first application image and the second application image is at least one of a hue, brightness, or a smoothing level, the first recognition result and the second recognition result being identical.

15. A training device, comprising:
an interface configured to acquire an input image; and
a processor including hardware and performing machine learning based on the input image;
the processor
generating a first augmented image by applying first data augmentation on the input image,
generating a second augmented image by applying, on the input image, second data augmentation different from the first data augmentation,
generating a first output by inputting the first augmented image to a neural network,
generating a second output by inputting the second augmented image to the neural network,
calculating an output difference indicating a degree of difference between the first output and the second output, and
updating a weight coefficient of each layer of the neural network based on the output difference.

16. An image processing device, comprising:
a memory configured to store a trained model;
a processor including hardware and performing image processing on an application image based on the trained model,
the trained model being trained by
generating a first augmented image by applying first data augmentation on an input image,
generating a second augmented image by applying, on the input image, second data augmentation different from the first data augmentation, generating a first output by inputting the first augmented image to a neural network, generating a second output by inputting the second augmented image to the neural network, calculating an output difference indicating a degree of difference between the first output and the second output, and updating a weight coefficient of each layer of the neural network based on the output difference.

17. The image processing device as defined in claim 16, the processor acquiring an in-vivo image captured by an endoscope apparatus as the application image and inputting the in-vivo image to the trained model to perform a recognition process targeting the in-vivo image.

* * * * *